United States Patent
Andersen

(10) Patent No.: US 9,669,078 B2
(45) Date of Patent: Jun. 6, 2017

(54) PD-L1 BASED IMMUNOTHERAPY

(71) Applicant: Herlev Hospital, Herlev (DK)

(72) Inventor: Mads Hald Andersen, Nærum (DK)

(73) Assignee: Herlev Hospital, Herlev (DK)

( * ) Notice: Subject to any disclaimer, the term of this patent is extended or adjusted under 35 U.S.C. 154(b) by 206 days.

(21) Appl. No.: 14/352,407

(22) PCT Filed: Oct. 17, 2012

(86) PCT No.: PCT/DK2012/050386
§ 371 (c)(1),
(2) Date: Apr. 17, 2014

(87) PCT Pub. No.: WO2013/056716
PCT Pub. Date: Apr. 25, 2013

(65) Prior Publication Data
US 2014/0242101 A1 Aug. 28, 2014

(30) Foreign Application Priority Data

Oct. 17, 2011 (DK) .................................. 201170574

(51) Int. Cl.
| | |
|---|---|
| *A61K 38/04* | (2006.01) |
| *A61K 38/17* | (2006.01) |
| *C07K 9/00* | (2006.01) |
| *C07K 14/00* | (2006.01) |
| *A61K 39/00* | (2006.01) |

(52) U.S. Cl.
CPC ...... *A61K 39/0005* (2013.01); *A61K 39/0008* (2013.01)

(58) Field of Classification Search
None
See application file for complete search history.

(56) References Cited

U.S. PATENT DOCUMENTS

| | | | | |
|---|---|---|---|---|
| 2003/0044768 A1* | 3/2003 | Wood | ................... | G01N 33/505 435/4 |
| 2009/0297518 A1* | 12/2009 | Honjo | ................ | A61K 31/7088 424/133.1 |
| 2011/0081341 A1* | 4/2011 | Honjo | ................ | A61K 31/7088 424/133.1 |

FOREIGN PATENT DOCUMENTS

| | | |
|---|---|---|
| WO | WO-2002086083 | 10/2002 |
| WO | WO-2008085562 | 7/2008 |
| WO | WO-2009026472 | 2/2009 |
| WO | WO-2010027828 | 3/2010 |
| WO | WO-2011066342 | 6/2011 |
| WO | WO-2011109789 | 9/2011 |

OTHER PUBLICATIONS

Sharpe et al., Nature Immunology 2007, 8: 239-245.*
Metzler et al., Nature Structural Biol. 1997; 4:527-531.*
Lederman et al., Molecular Immunology, 1991, 28: 1171-1181.*
Rentero et al., Chimia 2011, 65: 843-845.*
Colman et al., Research in Immunology, 1994, 145: 33-36.*
Andersen, M. et al., Identification of a Cytotoxic T Lymphocyte Response to the Apoptosis Inhibitor Protein Surviving in Cancer Patients, *Cancer Res*, 61: 869-872, 2001.
Benavides, L. et al., Comparison of different HER2/neu vaccines in adjuvant breast cancer trials: implications for dosing of peptide vaccines, *Expert Review of Vaccines*, 10(2): 201-210, 2011.
Francisco, L. et al., The PD-1 pathway in tolerance and autoimmunity, *Immunological Reviews*, 136(1), 219-242, 2010.
Hamanishi, J. et al., Programmed cell death 1 ligand 1 and tumor-infiltrating CD8(+) T lymphocytes are prognostic factors of human ovarian cancer, *Proceedings of the National Academy of Sciences*, 104(9): 3360-3365, 2007.
Hino, R. et al., Tumor Cell Expression of Programmed Cell Death-1 Ligand 1 is a prognostic factor for malignant melanoma, *Cancer*, 116(7): 1757-1766, 2010.
Jurado, J. et al., Programmed death (PD)-1: PD-ligand 2 pathway inhibits T cell effector functions during human tuberculosis, *Journ of Immun.*, 181(1): 116-125, 2008.
Nomi, T. et al, Clinical significance and therapeutic potential of the programmed death-1 ligand/programmed death-1 pathway in human pancreatic cancer; *Clinical Cancer Research*, 13(7), 2151-2157, 2007.
Stanciu, L. et al, Expression of programmed death-1 ligand (PD-L) 1, PD-L2, B7-H3, and inducible costimlator ligand on human respiratory tract epithelial cells and regulation by respiratory syncytial virus and type 1 and 2 cytokines, *Journ of infectious Diseases*, 193(3): 404-412, 2006.
Thompson, R. et al., Costimulatory B7-H1 in renal cell carcinoma patients: Indicator of tumor aggressiveness and potential therapeutic target, *Proceedings of the National Academy of Sciences*, 101(49): 17174-17179, 2004.

* cited by examiner

*Primary Examiner* — Ilia Ouspenski
(74) *Attorney, Agent, or Firm* — Dinsmore & Shohl LLP

(57) ABSTRACT

The present invention relates to the field of prophylaxis and therapy of clinical conditions including cancer, autoimmune diseases and infectious diseases. In particular there is provided vaccine compositions comprising PD-L1 or peptide fragments thereof that are capable of eliciting immune responses useful in treatment of cancer, autoimmune diseases or infectious diseases.

15 Claims, 19 Drawing Sheets

SEQUENCE LISTING

```
<160> NUMBER OF SEQ ID NOS: 28

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15
```

-continued

```
Asn Ala Phe Thr Val Thr Val Pro Lys Asp Leu Tyr Val Val Glu Tyr
         20                  25                  30
Gly Ser Asn Met Thr Ile Glu Cys Lys Phe Pro Val Glu Lys Gln Leu
         35                  40                  45
Asp Leu Ala Ala Leu Ile Val Tyr Trp Glu Met Glu Asp Lys Asn Ile
 50                  55                  60
Ile Gln Phe Val His Gly Glu Asp Leu Lys Val Gln His Ser Ser
 65                  70                  75                  80
Tyr Arg Gln Arg Ala Arg Leu Leu Lys Asp Gln Leu Ser Leu Gly Asn
                 85                  90                  95
Ala Ala Leu Gln Ile Thr Asp Val Lys Leu Gln Asp Ala Gly Val Tyr
                100                 105                 110
Arg Cys Met Ile Ser Tyr Gly Gly Ala Asp Tyr Lys Arg Ile Thr Val
            115                 120                 125
Lys Val Asn Ala Pro Tyr Asn Lys Ile Asn Gln Arg Ile Leu Val Val
130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Thr Asn Glu Ile Phe Tyr
        195                 200                 205
Cys Thr Phe Arg Arg Leu Asp Pro Glu Glu Asn His Thr Ala Glu Leu
210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
            260                 265                 270
Gly Ile Gln Asp Thr Asn Ser Lys Lys Gln Ser Asp Thr His Leu Glu
        275                 280                 285
Glu Thr
    290

<210> SEQ ID NO 2
<211> LENGTH: 9
<212> TYPE: PRT
<213> ORGANISM: artificial
<220> FEATURE:
<223> OTHER INFORMATION: PD-L1 peptide

<400> SEQUENCE: 2

Leu Leu Asn Ala Phe Thr Val Thr Val
1               5

<210> SEQ ID NO 3
<211> LENGTH: 9
<212> TYPE: PRT
<213> ORGANISM: artificial
<220> FEATURE:
<223> OTHER INFORMATION: PD-L1 peptide

<400> SEQUENCE: 3

Ile Leu Leu Cys Leu Gly Val Ala Leu
```

```
<210> SEQ ID NO 4
<211> LENGTH: 9
<212> TYPE: PRT
<213> ORGANISM: artificial
<220> FEATURE:
<223> OTHER INFORMATION: PD-L1 peptide

<400> SEQUENCE: 4

Ile Leu Gly Ala Ile Leu Leu Cys Leu
1               5

<210> SEQ ID NO 5
<211> LENGTH: 9
<212> TYPE: PRT
<213> ORGANISM: artificial
<220> FEATURE:
<223> OTHER INFORMATION: PD-L1 peptide

<400> SEQUENCE: 5

Ala Leu Gln Ile Thr Asp Val Lys Leu
1               5

<210> SEQ ID NO 6
<211> LENGTH: 9
<212> TYPE: PRT
<213> ORGANISM: artificial
<220> FEATURE:
<223> OTHER INFORMATION: PD-L1 peptide

<400> SEQUENCE: 6

Lys Leu Phe Asn Val Thr Ser Thr Leu
1               5

<210> SEQ ID NO 7
<211> LENGTH: 9
<212> TYPE: PRT
<213> ORGANISM: artificial
<220> FEATURE:
<223> OTHER INFORMATION: PD-L1 peptide

<400> SEQUENCE: 7

Arg Leu Leu Lys Asp Gln Leu Ser Leu
1               5

<210> SEQ ID NO 8
<211> LENGTH: 9
<212> TYPE: PRT
<213> ORGANISM: artificial
<220> FEATURE:
<223> OTHER INFORMATION: PD-L1 peptide

<400> SEQUENCE: 8

Gln Leu Ser Leu Gly Asn Ala Ala Leu
1               5

<210> SEQ ID NO 9
<211> LENGTH: 9
<212> TYPE: PRT
<213> ORGANISM: artificial
<220> FEATURE:
<223> OTHER INFORMATION: PD-L1 peptide

<400> SEQUENCE: 9

Lys Ile Asn Gln Arg Ile Leu Val Val
1               5
```

<210> SEQ ID NO 10
<211> LENGTH: 9
<212> TYPE: PRT
<213> ORGANISM: artificial
<220> FEATURE:
<223> OTHER INFORMATION: PD-L1 peptide

<400> SEQUENCE: 10

His Leu Val Ile Leu Gly Ala Ile Leu
1               5

<210> SEQ ID NO 11
<211> LENGTH: 9
<212> TYPE: PRT
<213> ORGANISM: artificial
<220> FEATURE:
<223> OTHER INFORMATION: PD-L1 peptide

<400> SEQUENCE: 11

Arg Ile Asn Thr Thr Thr Asn Glu Ile
1               5

<210> SEQ ID NO 12
<211> LENGTH: 9
<212> TYPE: PRT
<213> ORGANISM: artificial
<220> FEATURE:
<223> OTHER INFORMATION: PD-L1 peptide

<400> SEQUENCE: 12

Cys Leu Gly Val Ala Leu Thr Phe Ile
1               5

<210> SEQ ID NO 13
<211> LENGTH: 9
<212> TYPE: PRT
<213> ORGANISM: artificial
<220> FEATURE:
<223> OTHER INFORMATION: PD-L1 peptide

<400> SEQUENCE: 13

Gln Leu Asp Leu Ala Ala Leu Ile Val
1               5

<210> SEQ ID NO 14
<211> LENGTH: 9
<212> TYPE: PRT
<213> ORGANISM: artificial
<220> FEATURE:
<223> OTHER INFORMATION: PD-L1 peptide

<400> SEQUENCE: 14

Ser Leu Gly Asn Ala Ala Leu Gln Ile
1               5

<210> SEQ ID NO 15
<211> LENGTH: 10
<212> TYPE: PRT
<213> ORGANISM: artificial
<220> FEATURE:
<223> OTHER INFORMATION: PD-L1 peptide

<400> SEQUENCE: 15

Val Ile Leu Gly Ala Ile Leu Leu Cys Leu
1               5                   10

<210> SEQ ID NO 16
<211> LENGTH: 10
<212> TYPE: PRT
<213> ORGANISM: artificial
<220> FEATURE:
<223> OTHER INFORMATION: PD-L1 peptide

<400> SEQUENCE: 16

His Thr Ala Glu Leu Val Ile Pro Glu Leu
1               5                   10

<210> SEQ ID NO 17
<211> LENGTH: 10
<212> TYPE: PRT
<213> ORGANISM: artificial
<220> FEATURE:
<223> OTHER INFORMATION: PD-L1 peptide

<400> SEQUENCE: 17

Phe Ile Phe Met Thr Tyr Trp His Leu Leu
1               5                   10

<210> SEQ ID NO 18
<211> LENGTH: 10
<212> TYPE: PRT
<213> ORGANISM: artificial
<220> FEATURE:
<223> OTHER INFORMATION: PD-L1 peptide

<400> SEQUENCE: 18

Val Ile Trp Thr Ser Ser Asp His Gln Val
1               5                   10

<210> SEQ ID NO 19
<211> LENGTH: 9
<212> TYPE: PRT
<213> ORGANISM: artificial
<220> FEATURE:
<223> OTHER INFORMATION: HLA-A2 binding peptide

<400> SEQUENCE: 19

Asn Leu Val Pro Met Val Ala Thr Val
1               5

<210> SEQ ID NO 20
<211> LENGTH: 9
<212> TYPE: PRT
<213> ORGANISM: artificial
<220> FEATURE:
<223> OTHER INFORMATION: HLA-A2 binding peptide

<400> SEQUENCE: 20

Ile Leu Lys Glu Pro Val His Gly Val
1               5

<210> SEQ ID NO 21
<211> LENGTH: 25
<212> TYPE: RNA
<213> ORGANISM: artificial
<220> FEATURE:
<223> OTHER INFORMATION: PD-L1 siRNA primer

<400> SEQUENCE: 21
ccuacuggca uuugcugaac gcauu                                    25

<210> SEQ ID NO 22

```
<211> LENGTH: 25
<212> TYPE: RNA
<213> ORGANISM: artificial
<220> FEATURE:
<223> OTHER INFORMATION: PD-L1 siRNA primer

<400> SEQUENCE: 22
aaugcguuca gcaaaugcca guagg                                           25

<210> SEQ ID NO 23
<211> LENGTH: 19
<212> TYPE: PRT
<213> ORGANISM: Artificial Sequence
<220> FEATURE:
<223> OTHER INFORMATION: PD-L1 peptide

<400> SEQUENCE: 23

Phe Met Thr Tyr Trp His Leu Leu Asn Ala Phe Thr Val Thr Val Pro
1               5                   10                  15

Lys Asp Leu

<210> SEQ ID NO 24
<211> LENGTH: 23
<212> TYPE: PRT
<213> ORGANISM: Artificial Sequence
<220> FEATURE:
<223> OTHER INFORMATION: PD-L1 peptide

<400> SEQUENCE: 24

Val Ile Leu Gly Ala Ile Leu Leu Cys Leu Gly Val Ala Leu Thr Phe
1               5                   10                  15

Ile Phe Arg Leu Arg Lys Gly
            20

<210> SEQ ID NO 25
<211> LENGTH: 9
<212> TYPE: PRT
<213> ORGANISM: Artificial Sequence
<220> FEATURE:
<223> OTHER INFORMATION: CMV IE1 peptide

<400> SEQUENCE: 25

Val Leu Glu Glu Thr Ser Val Met Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Flu matrix p peptide

<400> SEQUENCE: 26

Gly Ile Leu Gly Phe Val Phe Thr Leu
1               5

<210> SEQ ID NO 27
<211> LENGTH: 10
<212> TYPE: PRT
<213> ORGANISM: Artificial Sequence
<220> FEATURE:
<223> OTHER INFORMATION: MART-1 peptide

<400> SEQUENCE: 27

Glu Ala Ala Gly Ile Gly Ile Leu Thr Val
1               5                   10
```

```
<210> SEQ ID NO 28
<211> LENGTH: 9
<212> TYPE: PRT
<213> ORGANISM: Artificial Sequence
<220> FEATURE:
<223> OTHER INFORMATION: UV sensititive ligand
<220> FEATURE:
<221> NAME/KEY: misc_feature
<222> LOCATION: (8)..(8)
<223> OTHER INFORMATION: Xaa can be any naturally occurring amino acid

<400> SEQUENCE: 28

Lys Ile Leu Gly Phe Val Phe Xaa Val
1               5
```

PD-L1 BASED IMMUNOTHERAPY

All patent and non-patent references cited in the application, or in the present application, are also hereby incorporated by reference in their entirety.

FIELD OF INVENTION

The present invention relates to the field of prophylaxis and therapy of clinical conditions including cancer, autoimmune diseases and infectious diseases. In particular there is provided vaccine compositions comprising PD-L1 or peptide fragments thereof that are capable of eliciting immune responses useful in treatment of cancer, autoimmune diseases or infectious diseases.

BACKGROUND OF INVENTION

The immune system has the capacity to recognize and destroy neoplastic cells; nevertheless, despite the fact that neoplastic transformation is associated with the expression of immunogenic antigens, the immune system often fails to respond effectively to these antigens. The immune system becomes tolerant towards these antigens. When this happens, the neoplastic cells proliferate uncontrollably leading to the formation of malignant cancers with poor prognosis for the affected individuals. The acquired state of tolerance must be overcome for cancer immunotherapy to succeed.

Several lines of evidence suggest that T cells are the main effectors in the immunological response against cancer cell. Immune regulatory proteins like indoleamine 2,3-dioxygenase (IDO), Cytotoxic T lymphocyte antigen 4 (CTLA-4) and Programmed cell death 1 ligand 1 (PD-L1) play a vital role in the immune suppression and tolerance induction of anti-cancer immune responses. CTLA-4 is a key negative regulator of T-cell responses, which can restrict the antitumor immune response. Recently, the anti-CTLA-4 antibody ipilimumab was approved by the FDA as well as EMEA for the treatment of melanoma after showing effect in clinical phase III studies. Another central mechanism counteracting tumor-specific immunity and preventing effective anticancer immunotherapy requires a specific environment in which tolerogenic dendritic cells (DC) play an essential role deviating the immune response away from effective immunity.

Programmed death-1 (PD1) is a regulatory surface molecule delivering inhibitory signals important to maintain T-cell functional silence against their cognate antigens. Its ligands, known as PD-L1 and PD-L2, or B7-H1 and B7-H2 are expressed on APCs, tumor cells, placental, and nonhematopoietic cells found in an inflammatory microenvironment. Interference with PD-1 or its ligand PD-L1 increases antitumor immunity. It appears that upregulation of PD-L1 is a mechanism that cancers can employ to evade the host immune system. Expression of PD-L1 on tumors correlates with poor clinical outcome for a number of cancers including pancreas, renal cell, ovarian, head and neck, and melanoma (Hamanishi et al., 2007, Proc. Natl. Acad. Sci. U.S.A. 104:3360-3365; Nomi et al., 2007, Clin. Cancer Res. 13:2151-2157; Hino et al., 2010, Cancer. 116:1757-1766. Thus, analysis of 196 tumor specimens from patients with renal cell carcinoma found that high tumor expression of PD-L1 was associated with increased tumor aggressiveness and a 4.5-fold increased risk of death (Thompson et al., 2004, Proc. Natl. Acad. Sci. U.S.A. 101:17174-17179). Ovarian cancer patients with higher expression of PD-L1 had a significantly poorer prognosis than those with lower expression of PD-L1. An inverse correlation was observed between PD-L1 expression and intraepithelial CD8+ T-lymphocyte count, suggesting that PD-L1 on tumor cells may suppress antitumor CD8+ T cells (Hamanishi et al., 2007, vide supra).

SUMMARY OF INVENTION

The problem of cancer immunosuppression is solved by the present invention which is based on the surprising finding by the inventors of spontaneous cytotoxic immune responses against PD-L1 expressing cells in cancer patients. These findings open the way for novel therapeutic and diagnostic approaches which may be generally applicable in the control of cancer diseases.

Interestingly, the findings are not restricted to cancer but are also useful in other clinical conditions characterized by the presence of undesired cells expressing PD-L1.

The present invention targets the cancer disease by killing the PD-L1 expressing cancer cells directly and by killing the PD-L1 expressing regulatory cells. This is done by enabling the T cells to recognize the PD-L1 expressing cells. Likewise, when the clinical condition is an infection, T cells are enabled to kill PD-L1 expressing APCs/DCs.

Thus, the expression of the immune suppressing enzyme PD-L1 in cancer cells and APCs is positive in conjunction with the application of the method of the present invention, which targets these PD-L1 expressing cells. This approach, especially as it entails the killing of the APCs/DCs, goes against the common opinion in the field, where PD-L1 generally is attempted inhibited in order to remove the tolerizing milieu around the APCs/DCs while preserving these cells, which are considered required in order to launch an effective immune response.

Furthermore, the finding of spontaneous cytotoxic immune responses against PD-L1 expressing cells is particularly surprising since PD-L1 expressing cells antagonize the desired effects of other immunotherapeutic approaches. Therefore, a combination of PD-L1- and tumor-targeting immunotherapies is highly synergistic.

The presence of an in vivo T-cell response specific for PD-L1 demonstrates that cancer patients are capable of generating T-cell responses to PD-L1 in vivo in response to the presence of PD-L1 peptides. Thus, the two conditions for generating a T-cell response are met: the T cells are present in the cancer patient and they have the ability to expand, which are shown in the application as filed. It follows from the general knowledge in the field of immunology that providing additional PD-L1 protein or PD-L1 peptides will lead to generation of PD-L1 specific T-cell responses.

In contrast to membrane-bound antibodies on B cells, which can recognize antigen alone, the T-cells recognizes a complex ligand, comprising an antigenic peptide bound to a protein called the major histocompatibility complex (MHC). In man, this molecule is known as human leukocyte antigen (HLA). Class I HLA molecules sample peptides from protein-degradation inside the cell and present these at the cell surface to T cells. Hence, this enables T-cells to scan for cellular alterations. When a T cell encounters antigen in the context of a HLA molecule, it undergoes clonal expansion and differentiates into memory and various effector T cells. Hence, identification of a spontaneous immune response is evidence that an antigen is a T-cell target. It demonstrates that specific T-cells have already been activated and have expanded in vivo.

The ELISPOT method used in Examples 1 and 3 of the present application is a very sensitive assay that demonstrates the presence of in vivo immune responses and not of naïve T-cells. Likewise, Peptide-MHC-tetramers have been successfully used to identify and study T cells specific for tumor-associated antigens (TAA) that develop endogenously or after vaccination in patients. Tetramers have also been used to isolate and expand TAA-specific T cells for adoptive cellular immunotherapy. The present application demonstrates the presence of PD-L1-tetramer specific T-cells (see Example 3) which also demonstrates an ongoing PD-L1 response in vivo.

The present invention regards a vaccine composition comprising PD-L1 of SEQ ID NO: 1 or a functional homologue thereof at least 70% identical thereto or an immunogenically active peptide fragment comprising a consecutive sequence of at least 8 amino acids PD-L1 or said functional homologue thereof or a nucleic acid encoding said PD-L1, said functional homologue thereof or said peptide fragment; and an adjuvant for use as a medicament.

The synergistic effect of a combination of immunotherapies based on the above disclosed vaccine is provided for in the aspect of the invention which regards a kit-of-parts comprising the vaccine composition and a further immunostimulating composition.

The aspect of combining the vaccine of the present invention with other cancer treatments such as chemotherapeutic agents is also provided for herein.

The aspect of combining the vaccine of the present invention with other treatments against infections such as immunotherapies and/or antibiotics is also provided for herein.

It follows that a method of treating a clinical condition such as a cancer or infection by any of the means described above falls within the scope of the present invention; the means including administering to an individual suffering from the clinical condition an effective amount of the vaccine composition as disclosed above or a kit-of-parts comprising the aforementioned vaccine together with another immunostimulating composition and/or chemotherapeutic agent.

It is thus also an object of the present invention to use PD-L1 or an immunogenically active peptide fragment thereof comprising a consecutive sequence of said PD-L1 or a functional homologue thereof or the vaccine composition of above in the manufacture of a medicament for the treatment or prevention of a cancer disease.

DETAILED DESCRIPTION OF THE INVENTION

Figure 1:
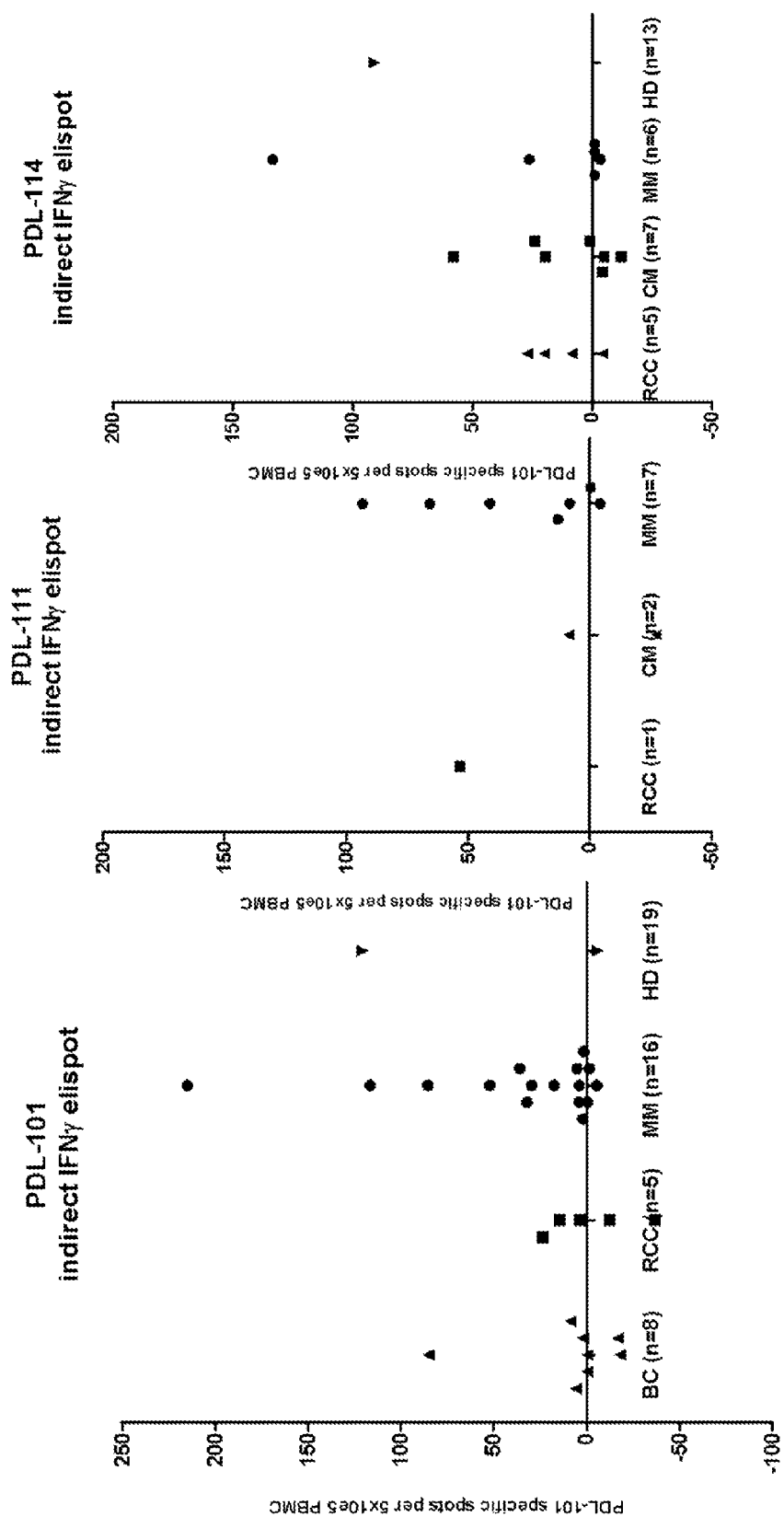
FIG. 1 shows the presence of T-cell responses against PDL101, PDL111 and PDL114 as measured by IFN-γ ELISPOT. The average number of PDL-specific spots (after subtraction of spots without added peptide) was calculated per $5 \times 10^5$ PBMC for each patient (white triangle). PBMC from breast cancer patients (BC), renal cell carcinoma patients (RCC), malignant melanoma patients (MM) as well as healthy individuals (HD) were analyzed. T cells were stimulated once with peptide before being plated at $5 \times 10^5$ cells per well in duplicates either without or with the PDL1 peptide.

It is a major objective of the present invention to provide a vaccine composition comprising PD-L1 or an immunologically active polypeptide fragment thereof for use as a medicament in the prevention of, reduction of risk from, or treatment of a clinical condition, wherein said clinical condition preferably is selected from the group consisting of cancer, infectious diseases and autoimmune diseases.

DEFINITIONS

Adjuvant: Any substance whose admixture with PD-L1 or an immunologically active peptide fragment thereof upon administration to an individual increases the immune response to PD-L1 or said peptide fragment thereof. Preferably said individual is a human being and preferably said immune response is a T-cell response.

Antibody: Immunoglobulin molecules and active portions of immunoglobulin molecules. Antibodies are for example intact immunoglobulin molecules or fragments thereof retaining the immunologic activity.

Antigen: Any substance that can bind to a clonally distributed immune receptor (T-cell or B-cell receptor). Usually a peptide, polypeptide or a multimeric polypeptide. Antigens are preferably capable of eliciting an immune response.

APC: Antigen-presenting cell. An APC is a cell that displays foreign antigen complexed with MHC on its surface. T-cells may recognize this complex using their T-cell receptor (TCR). APCs fall into two categories: professional, (of which there are three types: Dendritic cells, macrophages and B-cells) or non-professional (does not constitutively express the Major histocompatibility complex proteins required for interaction with naive T cells; these are expressed only upon stimulation of the non-professional APC by certain cytokines such as IFN-γ).

Boost: To boost by a booster shot or dose is to give an additional dose of an immunizing agent, such as a vaccine, given at a time after the initial dose to sustain the immune response elicited by the previous dose of the same agent.

Cancer: Herein any preneoplastic or neoplastic disease, benign or malignant, where "neoplastic" refers to an abnormal proliferation of cells.

Carrier: Entity or compound to which antigens are coupled to aid in the induction of an immune response.

Chimeric protein: A genetically engineered protein that is encoded by a nucleotide sequence made by a splicing together of two or more complete or partial genes or a series of (non)random nucleic acids.

Clinical condition: A condition that requires medical attention, herein especially conditions associated with the expression of PD-L1. Examples of such conditions include cancers, infectious diseases or autoimmune diseases.

CTL: Cytotoxic T lymphocyte. A sub group of T-cells expressing CD8 along with the T-cell receptor and therefore able to respond to antigens presented by class I molecules.

Cytokine: Growth or differentiation modulator, used non-determinative herein, and should not limit the interpretation of the present invention and claims. In addition to the cytokines, adhesion or accessory molecules, or any combination thereof, may be employed alone or in combination with the cytokines.

Delivery vehicle: An entity whereby a nucleotide sequence or polypeptide or both can be transported from at least one media to another.

DC: Dendritic cell. (DCs) are immune cells and form part of the mammalian immune system. Their main function is to process antigen material and present it on the surface to other cells of the immune system, thus functioning as antigen-presenting cells (APCs).

Fragment: is used to indicate a non-full length part of a nucleic acid or polypeptide. Thus, a fragment is itself also a nucleic acid or polypeptide, respectively.

Functional homologue: A functional homologue may be any polypeptide that exhibits at least some sequence identity with a wild type polypeptide and has retained at least one aspect of the wild type polypeptide's functionality. Herein a functional homologue of PD-L1 has the capability to induce a T-cell immune response to cells expressing PD-L1.

Individual: Generally any species or subspecies of bird, mammal, fish, amphibian, or reptile, preferably a mammal, most preferably a human being.

Infection: Herein the term "infection" relates to any kind of clinical condition giving rise to an immune response and therefore includes infections, chronic infections, autoimmune conditions and allergic inflammations.

Isolated: used in connection with nucleic acids, polypeptides, and antibodies disclosed herein 'isolated' refers to these having been identified and separated and/or recovered from a component of their natural, typically cellular, environment. Nucleic acids, polypeptides, and antibodies of the invention are preferably isolated, and vaccines and other compositions of the invention preferably comprise isolated nucleic acids, polypeptides or isolated antibodies.

MHC: Major histocompatibility complex, two main subclasses of MHC, Class I and Class II exist.

Nucleic acid construct: A genetically engineered nucleic acid. Typically comprising several elements such as genes or fragments of same, promoters, enhancers, terminators, polyA tails, linkers, polylinkers, operative linkers, multiple cloning sites (MCS), markers, STOP codons, other regulatory elements, internal ribosomal entry sites (IRES) or others.

Pathogen: a specific causative agent of disease, especially a biological agent such as a virus, bacteria, prion or parasite that can cause disease to its host, also referred to as an infectious agent.

PBMC: A Peripheral Blood Mononuclear Cell (PBMC) is a blood cell having a round nucleus, such as a lymphocyte or a monocyte. These blood cells are a critical component in the immune system to fight infection and adapt to intruders. The lymphocyte population consists of T cells (CD4 and CD8 positive ~75%), B cells and NK cells (~25% combined).

Pharmaceutical carriers: also termed excipients, or stabilizers are non-toxic to the cell or individual being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Plurality: At least two.

Promoter: A binding site in a DNA chain at which RNA polymerase binds to initiate transcription of messenger RNA by one or more nearby structural genes.

Treg: Regulatory T cells/T lymphocytes

Vaccine: A substance or composition capable of inducing an immune response in an animal. Vaccines are also referred to as "vaccine compositions" or as "immunogenic compositions" in the present text. Said immune response is according to the present invention preferably a T-cell response. A vaccine of the present invention may be given as or prophylactic and/or therapeutic medicament.

Variant: a 'variant' of a given reference nucleic acid or polypeptide refers to a nucleic acid or polypeptide that displays a certain degree of sequence identity to said reference nucleic acid or polypeptide but is not identical to said reference nucleic acid or polypeptide.

PD-L1

PD-L1 according to the present invention is a ligand of "Programmed cell Death 1". Human PD-L1 is PD-L1 is expressed at high levels in cancer cells, as well as in regulatory T-cells. Accordingly the vaccine compositions according to the present invention are useful for prophylaxis and/or treatment of clinical conditions characterized by the presence of undesired cells expressing high levels of PD-L1.

Therefore, not only cancer, but infections in general and infections, especially chronic infections as well as autoimmune diseases are all clinical conditions of relevance for the present invention.

Since PD-L1 expressing T-cells antagonize the desired effects of other immunotherapeutic approaches, targeting PD-L1-expressing cells e.g. by vaccination, consequently are highly synergistic in action with additional anti-cancer immunotherapy. In the present disclosure it is demonstrated that CTL defined PD-L1 epitopes are broadly applicable in therapeutic vaccinations and are therefore of substantial immunotherapeutic value.

It is thus an aspect of the present invention to provide a vaccine composition comprising PD-L1 or an immunologically active polypeptide fragment hereof for use as a medicament for the treatment of a clinical condition. Said clinical condition may be cancer and it is a further aspect of the present invention to prevent, reduce the risk from, or treat cancer. Another aspect relates to the use of the vaccine composition of the present invention in combination with other medicaments such as immunotherapeutic medicaments and/or chemotherapeutic agents. Yet an aspect relates to the use of a vaccine composition as herein disclosed for the treatment of diseases of viral and/or microbial origin and further to the use of said vaccine in combination with other medicaments such as immunotherapeutic medicaments and/or antibiotics and/or anti-viral agents.

The vaccine compositions according to the present invention comprise PD-L1 or an immunogenically active peptide fragment thereof for use in treatment of a clinical condition in an individual in need thereof. Preferably, said PD-L1 is PD-L1 of the species of said individual. Thus, if the individual in need thereof is a specific kind of mammal, said PD-L1 is preferably PD-L1 of said specific kind of mammal. In a preferred embodiment of the present invention the vaccine compositions comprises human PD-L1 of SEQ ID NO:1 or an immunigenically active peptide fragment thereof. The wild-type human PD-L1 i.e. the naturally occurring non-mutated version of the polypeptide is identified in SEQ ID NO: 1.

However, in certain embodiments of the invention the vaccine compositions of the invention comprise a functional homologue of PD-L1 or an immunologically active peptide fragment thereof as defined herein below.

The present invention thus relates to vaccine compositions comprising an adjuvant and:

i) PD-L1 of SEQ ID NO:1; or
ii) An immunologically active peptide fragment PD-L1 of SEQ ID NO:1; or
iii) A functional homologue of PD-L1 of SEQ ID NO:1 at least 70% identical thereto; or
iv) An immunogenically active peptide fragment of a functional homologue of PD-L1 of SEQ ID NO:1 at least 70% identical thereto, wherein said immunogenically active peptide fragment is an immunogenically active peptide fragment of PD-L1 of SEQ ID NO:1, wherein at the most three amino acids have been substituted, or
v) A nucleic acid encoding any of i) to iv)

The term peptide fragment of is used herein to define any non-full length (as compared to SEQ ID NO: 1) string of amino acid residues that are directly derived from or synthesized to be identical with a consecutive sting of amino acids of SEQ ID NO:1.

A functional homologue can be defined as a full length or fragment of PD-L1 that differs in sequence from the wild-type PD-L1, such as wild-type human PD-L1 of SEQ ID NO:1, but is still capable of inducing an immune response against PD-L1 expressing cells such as cancer cells and DCs. The PD-L1 expressed in these cells may be wild type or endogenously mutated (such as a congenital mutant or a mutation induced during cell division or other). A functional homologue may be a mutated version or an alternative splice variant of the wild-type PD-L1. In another aspect, functional homologues of PD-L1 are defined as described herein below. A functional homologue may be, but is not limited to, a recombinant version of full length or fragmented PD-L1 with one or more mutations and/or one or more sequence deletions and/or additions introduced ex vivo.

A functional homologue of PD-L1 may be any protein/polypeptide that exhibits at least some sequence identity with SEQ ID NO: 1 and has the capability to induce an immune response to cells expressing PD-L1.

Thus a functional homologue of PD-L1 according to the present invention preferably share at least 70% sequence identity to PD-L1 of SEQ ID NO: 1, and accordingly, functional homologue preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the sequence of human PD-L1 of SEQ ID NO:1 and has the capability of inducing an immune response to cells expressing PD-L1.

Sequence identity according to the present invention are determined over the entire reference sequence and thus sequence identity to SEQ ID NO:1 is determined over the entire length of SEQ ID NO:1. Sequence identity can be calculated using a number of well-known algorithms and applying a number of different gap penalties. The sequence identity is calculated relative to full-length SEQ ID NO: 1. Any sequence alignment tool, such as but not limited to FASTA, BLAST, or LALIGN may be used for searching homologues and calculating sequence identity. Moreover, sequence alignments may be performed using a range of penalties for gap opening and extension. For example, the BLAST algorithm may be used with a gap opening penalty in the range 5-12, preferably 8, and a gap extension penalty in the range 1-2, preferably 1.

Functional equivalents may further comprise chemical modifications such as ubiquitination, labeling (e.g., with radionuclides, various enzymes, etc.), pegylation (derivatization with polyethylene glycol), or by insertion (or substitution by chemical synthesis) of amino acids (amino acids) such as ornithine, which do not normally occur in human proteins, however it is preferred that the functional equivalent does not contain chemical modifications.

Any changes made to the sequence of amino acid residues compared to that of PD-L1 of SEQ ID NO: 1 are preferably conservative substitutions. A person skilled in the art will know how to make and assess 'conservative' amino acid substitutions, by which one amino acid is substituted for another with one or more shared chemical and/or physical characteristics. Conservative amino acid substitutions are less likely to affect the functionality of the protein. Amino acids may be grouped according to shared characteristics. A conservative amino acid substitution is a substitution of one amino acid within a predetermined group of amino acids for another amino acid within the same group, wherein the amino acids within a predetermined groups exhibit similar or substantially similar characteristics.

The immunogenically active peptide fragment of PD-L1 or the functional homologue thereof to be used with the invention may have any desired length. In a specific embodiment the immunogenically active peptide fragment of the invention consists of 50 amino acid residues or less, for example of at the most 45 amino acid residues, such as at the most 40 amino acid residues, for example at the most 35 amino acid residues, such as at the most 30 amino acid residues, for example at the most 25 amino acid residues, such as 18 to 25 consecutive amino acids of PD-L1 as identified in SEQ ID NO: 1 or a functional homologue thereof; the functional homologue being one wherein at the most three amino acids have been substituted, such as two amino acids, such as one amino acid has been substituted for another amino acid, preferably by conservative substitution.

Accordingly in another specific embodiment the immunogenically active peptide fragment of the invention consists of the most 25 amino acid residues, such as at the most 24 amino acid residues, such as at the most 23 amino acid residues, such as at the most 22 amino acid residues, such as at the most 21 amino acid residues, such as at the most 20 amino acid residues, for example at the most 19 amino acid residues, such as at the most 18 amino acid residues, for example at the most 17 amino acid residues, such as at the most 16 amino acid residues, for example at the most 15 amino acid residues, such as at the most 14 amino acid residues, for example at the most 13 amino acid residues, such as at the most 12 amino acid residues, for example at the most 11 amino acid residues, such as 8 to 10 consecutive amino acids from PD-L1 of SEQ ID no 1 or a functional homologue thereof; the functional homologue being one wherein at the most two amino acids, such as one amino acid has been substituted, preferably by conservative substitution. Preferably, the peptide comprises at the most 10 consecutive amino acid residues from PD-L1 of SEQ ID NO:1, such as 9 consecutive amino acid residues, such as 8 consecutive amino acid residues, such as 7 consecutive amino acid residues from PD-L1 as identified in SEQ ID NO: 1 or a functional homologue thereof; the functional homologue being one wherein at the most two amino acids, such as one amino acid has been substituted with another amino acid, preferably by conservative substitution.

Accordingly in some embodiments the immunogenically active peptide fragments of the invention are nonapeptides (peptides comprising 9 amino acid residues), and some decapeptides (comprising 10 residues).

In one preferred embodiment of the invention the immunogenically active peptide fragment comprises a peptide selected from the group consisting of the peptides listed in Table 1, more preferably a peptide selected from the group consisting of from the group of SEQ ID NO: 2, 12 and 15. Preferably, said immunogenically active peptide fragment consist of at the most 25 amino acid residues, such as at the most 24 amino acid residues, such as at the most 23 amino acid residues, such as at the most 22 amino acid residues, such as at the most 21 amino acid residues, such as at the most 20 amino acid residues, for example at the most 19 amino acid residues, such as at the most 18 amino acid residues, for example at the most 17 amino acid residues, such as at the most 16 amino acid residues, for example at the most 15 amino acid residues, such as at the most 14 amino acid residues, for example at the most 13 amino acid residues, such as at the most 12 amino acid residues, for example at the most 11 amino acid residues, such as of 10 amino acids, for example of 9 amino acids and comprises a peptide sequence selected from the group of peptides listed in Table 1, more preferably a peptide selected from the group consisting of from the group of SEQ ID NO: 2, 12 and 15.

In one very preferred embodiment of the invention said immunogenically active peptide fragment is selected from the group consisting peptides listed in Table 1, and more preferably selected from the group consisting of SEQ ID NO: 2, 12 and 15.

TABLE 1

| Peptide name | Amino acid Sequence | Start position in PD-L1 (SEQ ID NO: 1) | SEQ ID NO: |
|---|---|---|---|
| PDL101 | L L N A F T V T V | 15 | SEQ ID NO: 2 |
| PDL102 | I L L C L G V A L | 247 | SEQ ID NO: 3 |
| PDL103 | I L G A I L L C L | 243 | SEQ ID NO: 4 |
| PDL104 | A L Q I T D V K L | 98 | SEQ ID NO: 5 |
| PDL105 | K L F N V T S T L | 189 | SEQ ID NO: 6 |
| PDL106 | R L L K D Q L S L | 86 | SEQ ID NO: 7 |
| PDL107 | Q L S L G N A A L | 91 | SEQ ID NO: 8 |
| PDL108 | K I N Q R I L V V | 136 | SEQ ID NO: 9 |
| PDL109 | H L V I L G A I L | 240 | SEQ ID NO: 10 |
| PDL110 | R I N T T T N E I | 198 | SEQ ID NO: 11 |
| PDL111 | C L G V A L T F I | 250 | SEQ ID NO: 12 |
| PDL112 | Q L D L A A L I V | 47 | SEQ ID NO: 13 |
| PDL113 | S L G N A A L Q I | 93 | SEQ ID NO: 14 |
| PDL114 | V I L G A I L L C L | 242 | SEQ ID NO: 15 |
| PDL115 | H T A E L V I P E L | 220 | SEQ ID NO: 16 |
| PDL116 | F I F M T Y W H L L | 7 | SEQ ID NO: 17 |
| PDL117 | V I W T S S D H Q V | 165 | SEQ ID NO: 18 |

Other immunogenically active peptide fragments of the invention comprise (or more preferably consist of) between 4 and 120, preferably between 8 and 100, more preferably between 10 and 75, yet more preferably between 12 and 60, even more preferably between 15 and 40, such as between 18 and 25 contiguous amino acids of PD-L1 of SEQ ID NO: 1, wherein at the most three amino acids compared to the PD-L1 sequence of SEQ ID NO: 1 have been substituted, deleted or added, such as two amino acids have been substituted, deleted or added, or one amino acid has been substituted, deleted or added.

Thus, in an embodiment of the present invention, the vaccine composition comprises an immunigenically active peptide fragment consisting of a consecutive sequence of PD-L1 of SEQ ID NO: 1 in the range of 8 to 50 amino acids, preferably in the range of 8 to 10 or 20 to 25 amino acids, wherein at the most three amino acid has been substituted, and where the substitution preferably is conservative.

MHC

There are two types of MHC molecules; MHC class I molecules and MHC class II molecules. MHC class I molecules are recognized by CD8 T-cells, which are the principal effector cells of the adaptive immune response. MHC class II molecules are mainly expressed on the surface of antigen presenting cells (APCs), the most important of which appears to be the dendritic cells. APCs stimulate naïve T-cells, as well as other cells in the immune system. They stimulate both CD8 T-cells and CD4 T-cells.

In one embodiment, there are provided novel MHC Class I-restricted peptide fragments consisting of 8-10 amino acids from PD-L1 of SEQ ID NO 1 or a functional homologue thereof, wherein at the most two amino acids of SEQ ID NO 1 have been substituted, which are characterized by having at least one of several features, one of which is the ability to bind to the Class I HLA molecule to which it is restricted at an affinity as measured by the amount of the peptide that is capable of half maximal recovery of the Class I HLA molecule ($C_{50}$ value) which is at the most 50 µM as determined by the assembly binding assay as described herein. This assembly assay is based on stabilization of the HLA molecule after loading of peptide to the peptide transporter deficient cell line T2. Subsequently, correctly folded stable HLA heavy chains are immunoprecipitated using conformation dependent antibodies and the peptide binding is quantitated. The peptides of this embodiment comprises (or more preferably consists of) at the most 200, preferably at the most 100, more preferably at the most 50, yet more preferably at the most 25, even more preferably at the most 20, yet even more preferably at the most 15, such as at the most 10, for example in the range of 8 to 10 contiguous amino acids of PD-L1 of SEQ ID NO 1 or a functional homologue thereof wherein at the most two amino acids of SEQ ID NO 1 have been substituted.

This assay provides a simple means of screening candidate peptides for their ability to bind to a given HLA allele molecule at the above affinity. In preferred embodiments, the peptide fragment of the invention in one having a $C_{50}$ value, which is at the most 30 µM, such as a $C_{50}$ value, which is at the most 20 µM including $C_{50}$ values of at the most 10 µM, at the most 5 µM and at the most 2 µM.

In another preferred embodiment, there are provided novel MHC Class II-restricted peptide fragments of PD-L1 of SEQ ID NO 1 or a functional homologue thereof, wherein at the most two amino acids of SEQ ID NO 1 have been substituted, (also referred to herein as "peptides"), which are characterized by having at least one of several features described herein below. The peptides of this embodiment comprises (or more preferably consists of) between 4 and 120, preferably between 8 and 100, more preferably between 10 and 75, yet more preferably between 12 and 60, even more preferably between 15 and 40, such as between 18 and 25 contiguous amino acids of PD-L1 of SEQ ID NO 1 of SEQ ID NO 1 or a functional homologue thereof, wherein at the most two amino acids of SEQ ID NO 1 have been substituted, Thus there are provided novel MHC Class I-restricted peptide fragments of 8-10 amino acids or novel MHC Class II-restricted peptide fragments of 18-25 amino acids of PD-L1 of SEQ ID NO 1 or a functional homologue thereof, wherein at the most two amino acids of SEQ ID NO 1 have been substituted, which are characterized by having at least one of several features described herein below, one of which is the ability to bind to the Class I or Class II HLA molecule to which it is restricted.

In particular embodiments there are provided peptide fragments, which is an MHC Class I-restricted peptide or an MHC class II-restricted peptide having at least one of the following characteristics:

(i) capable of eliciting INF-γ-producing cells in a PBMC population of a cancer patient at a frequency of at least 20 per $10^5$ PBMCs as determined by an ELISPOT assay, and/or (ii) capable of in situ detection in a tumor tissue of CTLs that are reactive with the epitope peptide.

(iii) capable of inducing the growth of PD-L1 specific T-cells in vitro.

More preferred peptides according to the present invention are peptides capable of raising a specific T-cell response as determined by an ELISPOT assay, for example the ELISPOT assay described in Example 1 herein below. Some peptides although they do not bind MHC class I or class II with high affinity, may still give rise to a T-cell response as determined by ELISPOT. Other peptides capable of binding MHC class I or class II with high affinity also give rise to a T-cell response as determined by ELISPOT. Both kinds of peptides are preferred peptides according to the invention.

Hence, preferred peptides according to the present invention are peptides capable of raising a specific T-cell response as measured by an ELISPOT assay, wherein more than 20 peptide specific spots per $10^8$ cells, more preferably per $10^7$, even more preferably per $10^6$, yet more preferably per $10^5$ cells are measured. In particular, preferred peptides according to the present invention are peptides capable of raising a specific T-cell response of more than 20 peptide specific spots per $10^8$ PBMC, more preferably per $10^7$, even more preferably per $10^6$, yet more preferably per $10^5$ PBMC, when measured by the ELISPOT assay described in Example 1 including stimulation once with peptide in vitro.

Most preferred peptides according to the present invention are peptides that are capable of eliciting a cellular immune response, preferably a T-cell response in an individual suffering from a clinical condition characterized by the expression of PD-L1, the clinical condition preferably being a cancer, an autoimmune disease or an infectious disease, and most preferably a cancer.

As described above, the HLA system represents the human major histocompatibility (MHC) system. Generally, MHC systems control a range of characteristics: transplantation antigens, thymus dependent immune responses, certain complement factors and predisposition for certain diseases. More specifically, the MHC codes for three different types of molecules, i.e. Class I, II and III molecules, which determine the more general characteristics of the MHC. Of these molecules, the Class I molecules are so-called HLA-A, HLA-B and HLA-C molecules that are presented on the surface of most nucleated cells and thrombocytes.

The peptides of the present invention are characterized by their ability to bind to (being restricted by) a particular MHC Class I HLA molecule. Thus, in one embodiment the peptide is one which is restricted by a MHC Class I HLA-A molecule including HLA-A1, HLA-A2, HLA-A3, HLA-A9, HLA-A10, HLA-A11, HLA-Aw19, HLA-A23(9), HLA-A24(9), HLA-A25(10), HLA-A26(10), HLA-A28, HLA-A29(w19), HLA-A30(w19), HLA-A31(w19), HLA-A32 (w19), HLA-Aw33(w19), HLA-Aw34(10), HLA-Aw36, HLA-Aw43, HLA-Aw66(10), HLA-Aw68(28), HLA-A69 (28). More simple designations are also used throughout the literature, where only the primary numeric designation is used, e.g. HLA-A19 or HLA-A24 instead of HLA-Aw19 and HLA-A24(49), respectively. In specific embodiments, the peptide of the invention is restricted a MHC Class I HLA species selected from the group consisting of HLA-A1, HLA-A2, HLA-A3, HLA-A11 and HLA-A24. In specific embodiment, the peptide of the invention is restricted a MHC Class I HLA species HLA-A2 or HLA-A3.

In further useful embodiments, the peptide of the invention is a peptide, which is restricted by a MHC Class I HLA-B molecule including any of the following: HLA-B5, HLA-B7, HLA-B8, HLA-B12, HLA-B13, HLA-B14, HLA-B15, HLA-B16, HLA-B17, HLA-B18, HLA-B21, HLA-Bw22, HLA-B27, HLA-B35, HLA-B37, HLA-B38, HLA-B39, HLA-B40, HLA-Bw41, HLA-Bw42, HLA-B44, HLA-B45, HLA-Bw46 and HLA-Bw47. In specific embodiments of the invention, the MHC Class I HLA-B species to which the peptide of the invention is capable of binding is selected from HLA-B7, HLA-B35, HLA-B44, HLA-B8, HLA-B15, HLA-B27 and HLA-B51.

In further useful embodiments, the peptide of the invention is a peptide, which is restricted by a MHC Class I HLA-C molecule including but not limited to any of the following: HLA-Cw1, HLA-Cw2, HLA-Cw3, HLA-Cw4, HLA-Cw5, HLA-Cw6, HLA-Cw7 and HLA-Cw1.

In further useful embodiments, the peptide of the invention is a peptide, which is restricted by a MHC Class II HLA molecule including but not limited to any of the following: HLA-DPA-1, HLA-DPB-1, HLA-DQA1, HLA-DQB1, HLA-DRA, HLA-DRB and all alleles in these groups and HLA-DM, HLA-DO.

The selection of peptides potentially having the ability to bind to a particular HLA molecule can be made by the alignment of known sequences that bind to a given particular HLA molecule to thereby reveal the predominance of a few related amino acids at particular positions in the peptides. Such predominant amino acid residues are also referred to herein as "anchor residues" or "anchor residue motifs". By following such a relatively simple procedure based on known sequence data that can be found in accessible databases, peptides can be derived from PD-L1, which are likely to bind to a specific HLA molecule. Representative examples of such analyses for a range of HLA molecules are given in the below table:

TABLE 2

| HLA allele | Position 1 | Position 2 | Position 3 | Position 5 | Position 6 | Position 7 | C-terminal |
|---|---|---|---|---|---|---|---|
| HLA-A1 | | T, S | D, E | | | L | Y |
| HLA-A2 | | L, M | | | V | | L, V |
| HLA-A3 | | L, V, M | F, Y | | | | K, Y, F |
| HLA-A11 | | V, I, F, Y | M, L, F, Y, I | | | | K, R |
| HLA-A23 | | I, Y | | | | | W, I |
| HLA-A24 | | Y | | I, V | F | | I, L, F |
| HLA-A25 | | M, A, T | I | | | | W |
| HLA-A26 | E, D | V, T, I, L, F | | | | I, L, V | Y, F |
| HLA-A28 | E, D | V, A, L | | | | | A, R |
| HLA-A29 | | E | | | | | Y, L |
| HLA-A30 | | Y, L, F, V | | | | | Y |
| HLA-A31 | | | L, M, F, Y | | | | R |
| HLA-A32 | | I, L | | | | | W |
| HLA-A33 | | Y, I, L, V | | | | | R |
| HLA-A34 | | V, L | | | | | R |
| HLA-A66 | E, D | T, V | | | | | R, K |
| HLA-A68 | E, D | T, V | | | | | R, K |
| HLA-A69 | | V, T, A | | | | | V, L |
| HLA-A74 | | T | | | | | V, L |
| HLA-B5 | | A, P | F, Y | | | | I, L |
| HLA-B7 | * | P | | | | | L, F |
| HLA-B8 | | | K | K, R | | | L |
| HLA-B14 | | R, K | | | | | L, V |
| HLA-B15 (B62) | | Q, L, K, P, H, V, I, M, S, T | | | | | F, Y, W |
| HLA-B17 | | | | | | | L, V |
| HLA-B27 | | R | | | | | Y, K, F, L |
| HLA-B35 | | P | | | | | I, L, M, Y |
| HLA-B37 | | D, E | | | | | I, L, M |
| HLA-B38 | | H | D, E | | | | F, L |
| HLA-B39 | | R, H | | | | | L, F |
| HLA-B40 (B60, 61) | | E | F, I, V | | | | L, V, A, W, M, T, R |
| HLA-B42 | | L, P | | | | | Y, L |
| HLA-B44 | | E | | | | | F, Y, W |
| HLA-B46 | | M, I, L, V | | | | | Y, F |
| HLA-B48 | | Q, K | | | | | L |
| HLA-B51 | | A, P, G | | | | | F, Y, I, V |
| HLA-B52 | | Q | F, Y | | | | I, V |
| HLA-B53 | | P | | | | | W, F, L |
| HLA-B54 | | P | | | | | |
| HLA-B55 | | P | | | | | A, V |
| HLA-B56 | | P | | | | | A, V |
| HLA-B57 | | A, T, S | | | | | F, W, Y |
| HLA-B58 | | A, T, S | | | | | F, W, Y |
| HLA-B67 | | P | | | | | L |
| HLA-B73 | | R | | | | | P |
| HLA-Cw1 | | A, L | | | | | L |
| HLA-Cw2 | | A, L | | | | | F, Y |
| HLA-Cw3 | | A, L | | | | | L, M |
| HLA-Cw4 | | Y, P, F | | | | | L, M, F, Y |
| HLA-Cw6 | | | | | | | L, I, V, Y |
| HLA-Cw6 | | Y | | | | | L, Y, F |
| HLA-Cw8 | | Y | | | | | L, I, |
| HLA-Cw16 | | A, L | | | | | L, V |

* In one embodiment there is no specific anchor residue for this position, however in a preferred embodiment the anchor residue is R or A.

Thus, as an example, nonapeptides potentially having the ability to bind to HLA-A3 would have one of the following sequences: Xaa-L-Y-Xaa-Xaa-Xaa-Xaa-Xaa-K, Xaa-L-Y-Xaa-Xaa-Xaa-Xaa-Xaa-Y; Xaa-L-Y-Xaa-Xaa-Xaa-Xaa-Xaa-F or Xaa-V-Y-Xaa-Xaa-Xaa-Xaa-Xaa-K (Xaa indicating any amino acid residue). In a similar manner, sequences potentially having the ability to bind to any other HLA molecule can be designed. It will be appreciated that the person of ordinary skill in the art will be able to identify further "anchor residue motifs" for a given HLA molecule.

The peptide of the invention may have a sequence which is a consecutive sequence of the native sequence of the PD-L1 of SEQ ID NO:1. However, peptides having a higher affinity to any given HLA molecule may be derived from such a native sequence by modifying the sequence by substituting, deleting or adding at least one amino acid residue, whereby anchor residue motifs in respect of the given HLA molecule are identified.

Thus, in useful embodiments, the polypeptides of the invention include peptides, the sequences of which comprise, for each of the specific HLA alleles listed in the table, any of the amino acid residues as indicated in the table.

Thus, the peptides of the invention may be any of the above-mentioned peptides comprising contiguous sequences from PD-L1, wherein in the range of 1 to 10, preferably in the range of 1 to 5, more preferably in the range of 1 to 3, even more preferably in the range of 1 to 2, yet more preferably 1 amino acid has been exchanged for another amino acid, preferably in a manner so that the peptide comprises one or more, preferably all anchor residues of a given HLA-A specific peptide as indicated in Table 2 above.

Examples preferable HLA species include, to which preferred peptides of the present invention are restricted include: a MHC Class I HLA species selected from the group consisting of HLA-A1, HLA-A2, HLA-A3, HLA-A11 and HLA-A24, more preferably the peptide is restricted by HLA-A3 or HLA-A2. Alternatively a preferred HLA species includes MHC Class I HLA-B species selected from the group consisting of HLA-B7, HLA-B35, HLA-B44, HLA-B8, HLA-B15, HLA-B27 and HLA-B51.

An approach to identifying polypeptides of the invention includes the following steps: selecting a particular HLA molecule, e.g. one occurring at a high rate in a given population, carrying out an alignment analysis as described above to identify "anchor residue motifs" in the PD-L1 protein, isolating or constructing peptides of a suitable size that comprise one or more of the identified anchor residues and testing the resulting peptides for the capability of the peptides to elicit INF-γ-producing cells in a PBMC population of a cancer patient at a frequency of at least 20 per $10^5$ PBMC as determined by an ELISPOT assay as described in Example 1 including a stimulation in vitro with peptide once.

In one aspect of the present invention, PD-L1-derived peptides longer than 8 to 10 amino acid residues are provided. Polypeptides longer than 8 to 10 amino acids are processed by the proteasome to a shorter length for binding to HLA molecules. Thus, when administering a polypeptide longer than 8 to 10 amino acid residues long, the "long" polypeptide/protein/protein fragment/variant of PD-L1 is processed into a series of smaller peptides in the cytosol by the proteasome. An advantage of using a longer polypeptide that may be processed by the proteasome into a variety of different shorter peptides is that more HLA classes may be targeted with one peptide than one 8 to 10 amino acid peptide that is restricted to a particular HLA class.

Surprisingly, some of the peptides of the present invention bind to MHC molecules with an affinity sufficiently high to render substitutions unnecessary and are ready for use as antigens as they are presented here. Preferably, the vaccine composition of the present invention comprises one or more of the following: PD-L1 full length polypeptide (SEQ ID NO: 1), polypeptide fragments here from, functional homologues of full length PD-L1 of SEQ ID NO:1 and immunigenically active peptide fragments of PD-L1 wherein one or two amino acids have been substituted, added or deleted. More preferably, the vaccine composition comprises any of the sequences listed in the sequence listing of the present disclosure. Very preferably, the vaccine composition comprises the peptides PDL101 (SEQ ID NO: 2), PDL111 (SEQ ID NO: 12), and/or PDL114 (SEQ ID NO: 15).

A significant feature of the peptide of the invention is its capability to recognize or elicit INF-γ-producing responder T cells, i.e. cytotoxic T cells (CTLs) that specifically recognize the particular peptide in a PBMC population, on an APC or tumor/neoplastic cells of an individual suffering from a cancer and/or an infection (target cells). This activity is readily determined by subjecting PBMCs, APCs or tumor cells from an individual to an ELISPOT assay. Prior to the assay, it may be advantageous to stimulate the cells to be assayed by contacting the cells with the peptide to be tested. Preferably, the peptide is capable of eliciting or recognizing INF-γ-producing T cells at a frequency of at least 20 per $10^5$ PBMCs as determined by an ELISPOT assay as used herein. More preferably the frequency is at least 30 per $10^5$ PBMCs.

The ELISPOT assay represents a strong tool to monitor PD-L1 specific T-cell responses. A major implication of the findings herein is that the peptides of the invention are expressed and complexed with HLA molecules on cancer cells and/or PD-L1 expressing APCs. This renders these cancer cells susceptible to destruction by CTLs and emphasizes the potential usefulness of PD-L1 immunization to fight cancer and infections. The presence of spontaneous CTL-responses in PBMCs from renal cell carcinoma patients, melanoma patients and breast cancer patients to HLA-restricted PD-L1 derived peptide epitopes shows the immunotherapeutic potential of PD-L1 immunogenic peptides.

In an embodiment of the present invention the immunigenically active peptide fragment of the invention is capable of inducing PD-L1 specific T-cells capable of killing cells, such as cancer cells expressing PD-L1. In particular it is preferred that said peptide fragment is capable of inducing PD-L1 specific T-cells capable of lysing at least 10% cancer cells, such as MDA-MB231 cells after co-incubation in vitro as described herein below in Example 1 and 2.

Origin

The protein from which the peptide can be derived can be any PD-L1 polypeptide from any animal species in which the protein is expressed. In preferred embodiments, the starting protein is from a mammalian species including a rodent species, rabbit and a primate species such as humans. Based on the sequence of the selected protein, the peptide of the invention is derived by any appropriate chemical or enzymatic treatment of the protein starting material that results in a peptide of a suitable size as indicated above, or it can be synthesized by any conventional peptide synthesis procedures with which the person of ordinary skills in the art is familiar. Most preferably, the PD-L1 polypeptide is human PD-L1 and more preferably human PD-L1 of SEQ ID NO:1.

Individual

The individual to be treated with the vaccine composition of the present invention is an individual suffering from a clinical condition. The individual is preferably of a mammalian species and most preferably a human being. The individual may be of any age, young or old, and may be either male or female. The clinical condition from which the individual suffers may be a neoplastic disease such as a cancer, or an infectious disease such as an intracellular infection or a viral infection or an autoimmune disease.

An embodiment of the present invention provides a vaccine for the treatment, reduction of risk of, stabilization of or prevention of a cancer. In another embodiment the present invention provides a vaccine for the treatment, reduction of risk of, stabilization of or prevention of a disease stemming from an infection, such as an intracellular infection or viral infection. In yet another embodiment the invention provides vaccine compositions for treatment, reduction of risk of, stabilization of or prevention of an autoimmune disease.

Cancer

The vaccine composition of the present invention may be used to prevent, reduce the risk from or treat a clinical condition. Preferably, the clinical condition is associated with or characterized by the expression of PD-L1. PD-L1 may be PD-L1 as identified in SEQ ID NO: 1 or a homolog sharing at least 70% identity with SEQ ID NO:1. It is understood hereby that the expression level of PD-L1 (the expression being expression of hnRNA, mRNA, precursor protein, fully processed protein and so on) is the same or higher than in an individual not suffering from said clinical condition.

In a preferred embodiment of the invention, the clinical condition is cancer. Cancer (malignant neoplasm) is a class of diseases in which a group of cells display the traits of uncontrolled growth (growth and division beyond the normal limits), invasion (intrusion on and destruction of adjacent tissues), and sometimes metastasis (spread to other locations in the body via lymph or blood). These three malignant properties of cancers differentiate them from benign tumors, which are self-limited, do not invade or metastasize. Most cancers form a tumor but some, like leukemia, do not. The term "cancer" as used herein is meant to encompass any cancer, neoplastic and preneoplastic disease.

A non-limiting group of cancers given as examples of cancers that may be treated, managed and/or prevented by administration of the vaccine of the present invention include: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In a preferred embodiment the vaccine composition according to the invention vaccine composition is capable of eliciting a clinical response in subject, wherein the clinical response may be characterized by a stable disease, in a preferred embodiment the clinical response may be characterized by a partial response or preferably the clinical response may be characterized by complete remission of a cancer. Preferably, the cancer is selected from the group of; melanoma, breast cancer, ovarian cancer, lung cancer, pancreatic cancer, hematologic cancers (such as leukemias), colon and renal cell cancers, more preferably from the group consisting of melanoma, renal cell cancer and breast cancer.

In one aspect of the invention the vaccine composition is capable of eliciting a clinical response in an individual. In one embodiment the clinical response may be characterized by a stable disease (no further worsening or progression), in a preferred embodiment the clinical response may be characterized by a partial response or preferably the clinical response may be characterized by complete remission of a cancer or infections. The clinical response may be determined as described herein below.

In another aspect of the invention the vaccine composition is capable of eliciting a clinical response in subject, wherein the clinical response is characterized by a decrease in the sum of the longest diameter of the largest target lesion. The decrease may be determined as described herein below.

All measurable lesions up to a maximum of five lesions per organ and 10 lesions in total, representative of all involved organs should be identified as target lesions and recorded and measured at baseline.

Target lesions should be selected on the basis of their size (lesions with the longest diameter) and their suitability for accurate repeated measurements (either by imaging techniques or clinically).

A sum of the longest diameter (LD) for all target lesions will be calculated and reported as the baseline sum LD. The baseline sum LD will be used as reference by which to characterize the objective tumor.

All other lesions (or sites of disease) should be identified as non-target lesions and should also be recorded at baseline. Measurements of these lesions are not required, but the presence or absence of each should be noted throughout follow-up.

Evaluation of Target Lesions

Complete Response (CR): Disappearance of all target lesions

Partial Response (PR): At least a 30% decrease in the sum of the LD of target lesions, taking as reference the baseline sum LD Progressive Disease (PD): At least a 20% increase in the sum of the LD of target lesions, taking as reference the smallest sum LD recorded since the treatment started or the appearance of one or more new lesions Stable Disease (SD): Neither sufficient shrinkage to qualify for PR nor sufficient increase to qualify for PD, taking as reference the smallest sum LD since the treatment started Evaluation of Non-Target Lesions Complete Response (CR): Disappearance of all non-target lesions and normalization of tumor marker level Incomplete Response/Stable Disease (SD): Persistence of one or more non-target lesion(s) or/and maintenance of tumor marker level above the normal limits Progressive Disease (PD): Appearance of one or more new lesions and/or unequivocal progression of existing non-target lesions In an embodiment of the present invention the vaccine composition comprising any of the herein mentioned proteins and/or polypeptides is capable of eliciting a clinical response in subject, wherein the clinical response is characterized by a decrease in the sum of the longest diameter of the largest target lesion It is contemplated that the vaccine composition of the invention is capable of eliciting an immune response against a cancer expressing PD-L1 of SEQ ID NO: 1 or a functional homologue thereof having at least 70% identity to SEQ PD-L1. The vaccine composition of the invention is capable of eliciting the production in a vaccinated individual of effector T-cells having a cytotoxic effect against the cancer cells, PD-L1 expressing APCs and/or inducing infiltration of antigen specific T-cells in tumor stroma in a subject.

In addition to their capacity to elicit immune responses in PBMC populations it is also contemplated that the peptides of the invention are capable of eliciting cytolytic immune responses in situ, i.e. in solid tumor tissues. This may for example be demonstrated by providing HLA-peptide complexes, e.g. being multimerized and being provided with a detectable label, and using such complexes for immunohistochemistry stainings to detect in a tumor tissue CTLs that are reactive with the immunogenically active peptide fragments of the invention. Accordingly, a further significant feature of the peptide of the invention is that it is capable of in situ detection in a tumor tissue of CTLs that are reactive with the epitope peptide.

It is also contemplated that the peptides of the invention, in addition to their capacity to bind to HLA molecules resulting in the presentation of complexes of HLA and peptides on cell surfaces, which complexes in turn act as epitopes or targets for cytolytic T cells, may elicit other types of immune responses, such as B-cell responses resulting in the production of antibodies against the complexes and/or a Delayed Type Hypersensitivity (DTH) reaction. The latter type of immune response is defined as a redness and palpable induration at the site of injection of the peptide of the invention.

It is an object of the present invention to provide a vaccine composition comprising PD-L1 of SEQ ID NO: 1 or a functional homologue thereof having at least 70% identity to SEQ ID NO: 1 or an immunogenically active peptide fragment comprising a consecutive sequence of said PD-L1 or said functional homologue thereof or a nucleic acid encoding said PD-L1 or said peptide fragment; and an adjuvant, for the prevention of, reduction of risk from or treatment of cancer.

Cancer Combination Treatment

In embodiments of the invention, wherein the invention relates to vaccine compositions comprising PD-L1 or an immunigenically active peptide fragment thereof for treatment of cancer, it may in some cases be appropriate to combine treatment with the vaccine composition according to the invention with a further conventional cancer treatment such as chemotherapy, radiotherapy, treatment with immunostimulating substances, gene therapy, treatment with antibodies and treatment using dendritic cells.

Since elevated expression of PD-L1 in tumor cells leads to inhibition of the immune system, the combination of a PD-L1-based immunotherapy as disclosed by the present invention with cytotoxic chemotherapy and or another anticancer immunotherapeutic treatment is an effective approach to treat cancer. These remedies are also referred to herein as "second active ingredients".

Examples of chemotherapeutic agents that are of relevance in regards to administration (sequentially or simultaneously) with the vaccine composition of the present invention include, but are not limited to: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

Another second active ingredient may be a kinase inhibitor, for separate, simultaneous or combined use in the treatment of tumors. Suitable kinase inhibitors include those which have been shown to possess anti-tumor activity (such as gefitinib (Iressa) and erlotinib (Tarceva) and these could be used in combination with the peptides. The receptor tyrosine kinase inhibitors, such as Sunitinib malate and Sorafenib which have been shown to be effective in the treatment of renal cell carcinoma are also suitable to be used as second active ingredients.

Further examples of second active ingredients are immunostimulating substances e.g. cytokines and antibodies. Such as cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In an embodiment, the vaccine composition of the present invention, comprising PD-L1, any of the functional homologues thereof described herein above or any of the immunigenically active peptide fragments thereof described herein above, is administered in combination with a second active ingredient, such as an immunostimulatory substance. The immunostimulatory substance is preferably an interleukin such as IL-21 or IL-2 or a chemotherapeutic agent.

Infectious Diseases and Autoimmune Diseases

The present invention also relates to vaccine compositions comprising PD-L1 or any of the immunogenically active peptide fragments thereof described herein above for the treatment of a clinical condition, wherein the clinical condition may be an infection or the clinical condition may be an autoimmune disease.

The word infection as used herein relates to any kind of clinical condition giving rise to an immune response, such as an inflammation, and therefore includes infectious diseases, chronic infections, autoimmune conditions and allergic inflammations. Thus, infections, such as infectious diseases, chronic infections, autoimmune conditions and allergic inflammations are all clinical conditions of relevance for the present invention, and are dealt with in turn hereunder.

In particular the infection or the autoimmune disease may be a disease associated with inflammation. Inflammation is the complex biological response of vascular tissues to harmful stimuli, such as pathogens, damaged cells, or irritants. It is a protective attempt by the organism to remove the injurious stimuli as well as initiate the healing process for the tissue. Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process. In either case, PD-L1 is expressed by cells of the immune system such as the APCs and therefore infections and inflammations are clinical conditions that may be treated, prevented, or from which the risk may be reduced by the administration of the vaccine composition of the present invention. The vaccine composition preferably comprises PD-L1 or any of the immunogenically active peptides fragments thereof described herein above.

Examples of disorders associated with inflammation which are of relevance to the presenting invention include, but are not limited to: Allergic inflammations, Asthma, Autoimmune diseases, Chronic inflammations, Chronic prostatitis, Glomerulonephritis, Hypersensitivities, Infectious diseases, Inflammatory bowel diseases, Pelvic inflammatory disease, Reperfusion injury, Rheumatoid arthritis, Transplant rejection, and Vasculitis.

Chronic Infections and Inflammations

In one embodiment of the present invention the clinical condition is a chronic inflammation. In particular, the autoimmune disease to be treated with the vaccine compositions of the invention may be a chronic inflammation. A chronic inflammation is a pathological condition characterized by concurrent active inflammation, tissue destruction, and attempts at repair. Chronically inflamed tissue is characterized by the infiltration of mononuclear immune cells (monocytes, macrophages, lymphocytes, and plasma cells), tissue destruction, and attempts at healing, which include angiogenesis and fibrosis.

In acute inflammation, removal of the stimulus halts the recruitment of monocytes (which become macrophages under appropriate activation) into the inflamed tissue, and existing macrophages exit the tissue via lymphatics. However in chronically inflamed tissue the stimulus is persistent, and therefore recruitment of monocytes is maintained, existing macrophages are tethered in place, and proliferation of macrophages is stimulated (especially in atheromatous plaques).

It is an object of the presenting invention to provide a vaccine composition comprising PD-L1 of SEQ ID NO: 1 or a functional homologue thereof having at least 70% identity to SEQ ID NO: 1 or an immunogenically active peptide fragment comprising a consecutive sequence of said PD-L1 or said functional homologue thereof, for example any of the immunogenically active peptide fragments described herein above or a nucleic acid encoding said PD-L1 or said peptide fragment; and an adjuvant, for the prevention of, reduction of risk from or treatment of an autoimmune disease, for example treatment of a chronic inflammation.

Infectious Diseases

The vaccine composition of the present invention may be used to prevent, reduce the risk from or treat a clinical condition. In a preferred embodiment of the invention, the clinical condition is an infectious disease. The infectious disease may be promoted by any infectious agent such as bacteria, virus, parasites and or fungi that are capable of inducing an increased expression of PD-L1 in the individual suffering from the infectious disease, preferably, the infectious disease is or is at risk of becoming a chronic disease. Therefore it is an aspect of the present invention to provide a vaccine composition comprising PD-L1 or any of the immunogenically active peptide fragment thereof described herein above for the treatment, amelioration of (lessening of severity) stabilization and/or prevention of a disease caused by an infectious agent.

An infectious diseases may be caused by a virus, and viral diseases against which the vaccine composition of the present invention may be administered in the treatment of include, but are not limited to the following viral diseases: HIV, AIDS, AIDS Related Complex, Chickenpox (Varicella), Common cold, Cytomegalovirus Infection, Colorado tick fever, Dengue fever, Ebola hemorrhagic fever, Hand, foot and mouth disease, Hepatitis, Herpes simplex, Herpes zoster, HPV (Human papillomavirus), Influenza (Flu), Lassa fever, Measles, Marburg hemorrhagic fever, Infectious mononucleosis, Mumps, Norovirus, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease, and Yellow fever. Preferably, the vaccine composition is administered to individuals suffering from HIV/AIDS or viral infections that may cause cancer. The main viruses associated with human cancers are human papillomavirus, hepatitis B and hepatitis C virus, Epstein-Barr virus, and human T-lymphotropic virus; thus it is an object of the present invention to be administered as the treatment of or as part of the treatment of these viral infections. More preferably, the infectious disease may be infection with a virus selected from the group consisting of HIV and Hepatitis virus.

Examples of bacterial infections of relevance for the present invention include, but are not limited to: Anthrax, Bacterial Meningitis, Botulism, Brucellosis, Campylobacteriosis, Cat Scratch Disease, Cholera, Diphtheria, Epidemic Typhus, Gonorrhea, Impetigo, Legionellosis, Leprosy (Hansen's Disease), Leptospirosis, Listeriosis, Lyme disease, Melioidosis, Rheumatic Fever, MRSA infection, Nocardiosis, Pertussis (VVhooping Cough), Plague, Pneumococcal pneumonia, Psittacosis, Q fever, Rocky Mountain Spotted Fever (RMSF), Salmonellosis, Scarlet Fever, Shigellosis, Syphilis, Tetanus, Trachoma, Tuberculosis, Tularemia, Typhoid Fever, Typhus, and Urinary Tract Infections. It is an object of the present invention to provide a vaccine for the treatment and/or prevention and/or reduction of risk from a bacterial infection.

It is a further aspect of the present invention to provide a vaccine composition for the treatment and/or prevention and/or reduction of risk from: Parasitic infectious diseases such as, but not limited to: African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trichomoniasis, and Trypanosomiasis; Fungal infectious diseases such but not limited to: Aspergillosis, Blastomycosis, Candidiasis, Coccidioidomycosis, Cryptococcosis, Histoplasmosis, Tinea pedis; Prion infectious diseases such but not limited to: transmissible spongiform encephalopathy, Bovine spongiform encephalopathy, Creutzfeldt-Jakob disease, Kuru-Fatal Familial Insomnia, and Alpers Syndrome; thus it is an object of the present invention to be administered as the treatment of or as part of the treatment of these parasitic, fungal or prion caused infections.

1. In a preferred embodiment the vaccine compositions of the invention are for treatment of an infectious disease, which is an intracellular infection, preferably in intracellular infection with a pathogen selected from the group consisting of *L. monocytogenes* and *plasmodium*.

Infectious Disease Combination Treatment

It is further provided for that a treatment of any infectious disease by the administration of the vaccine composition according to the present invention may be given in conjunction with a further (second) active ingredient either sequentially in any order or simultaneously or in combination with a further treatment such as antibiotic treatment, chemotherapy, treatment with immunostimulating substances, treatment using dendritic cells, antiviral agents anti parasitic agents and so forth.

Examples of a second active ingredient that may be used in the treatment of an infectious disease in combination with the vaccine of the present invention include, and are not limited to antibiotics. The term antibiotics herein refers to substances with anti-bacterial, anti-fungal, anti-viral and/or anti-parasitical activity; examples of relevance to the present invention include, but are not limited to: Amikacin, Gentamycin, Kanamycin, Neomycin, Netilmicin, Paromomycin, Streptomycin, Tobramycin, Ertapenem, Imipenem, Meropenem, Chloramphenicol, Fluoroquinolones, Ciprofloxacin, Gatifloxacin, Gemifloxacin, Grepafloxacin, Levofloxacin, Lomefloxacin, Moxifloxacin, Norfloxacin, Ofloxacin, Sparfloxacin, Trovafloxacin, Glycopeptides, Vancomycin, Lincosamides, Clindamycin, Macrolides/Ketolides, Azithromycin, Clarithromycin, Dirithromycin, Erythromycin, Cefadroxil, Cefazolin, Cephalexin, Cephalothin, Cephapirin, Cephradine, Cefaclor, Cefamandole, Cefonicid, Cefotetan, Cefoxitin, Cefprozil, Cefuroxime, Loracarbef, Cefdinir, Cefditoren, Cefixime, Cefoperazone, Cefotaxime, Cefpodoxime, Ceftazidime, Ceftibuten, Ceftizoxime, Ceftriaxone, Cefepime, Monobactams, Aztreonam, Nitroimidazoles, Metronidazole, Oxazolidinones, Linezolid, Penicillins, Amoxicillin, Amoxicillin/Clavulanate, Ampicillin, Sulbactam, Bacampicillin, Carbenicillin, Cloxacillin, Dicloxacillin, Methicillin, Mezlocillin, Nafcillin, Oxacillin, Penicillin G, Penicillin V, Piperacillin, Piperacillin/Tazobactam, Ticarcillin, Ticarcillin/Clavulanate, Streptogramins, Quinupristin, Dalfopristin, Sulfonamide/Sulfamethoxazole, Trimethoprim, Tetracyclines, Demeclocycline, Doxycycline, Minocycline, Tetracycline, Azole antifungals Clotrimazole Fluconazole, Itraconazole, Ketoconazole, Miconazole, Voriconazole, Amphotericin B, Nystatin, Echinocandin, Caspofungin, Micafungin, Ciclopirox, Flucytosine, Griseofulvin, and Terbinafine. Of further relevance are antivirals such as Vidarabine, Acyclovir, Gancyclovir and Valcyte (valganciclovir), Nucleoside-analog reverse transcriptase inhibitors (NRTI): AZT (Zidovudine), ddI (Didanosine), ddC (Zalcitabine), d4T (Stavudine), 3TC (Lamivudine), Non-nucleoside reverse transcriptase inhibitors (NNRTI): Nevirapine, Delavirdine, Protease Inhibitors Saquinavir, Ritonavir, Indinavir, Nelfinavir, Ribavirin, Amantadine/Rimantadine, Relenza and Tamiflu, Pleconaril, Interferons In an embodiment, the present invention regards a vaccine composition comprising PD-L1 of SEQ ID NO:1, any of the functional homologues thereof described herein above or any of the immunigenically active peptide fragments thereof described herein above for the treatment of an infectious disease in combination with at least one antibiotic. Preferably, the vaccine composition of the present invention is used for the treatment of chronic infections e.g. HIV and therefore is used in combination with any of the above listed antibiotics such as anti-viral agents.

Autoimmune Diseases

Autoimmune diseases arise when an organism fails to recognize its own constituent parts (down to the sub-molecular levels) as self, which results in an immune response against its own cells and tissues. Any disease that results from such an aberrant immune response is termed an autoimmune disease and is of relevance to the present invention.

It is an object of the present invention to provide a vaccine composition comprising PD-L1 of SEQ ID NO: 1 or a functional homologue thereof having at least 70% identity to SEQ ID NO: 1 or any immunogenically active peptide fragments of PD-L1 described herein above or a nucleic acid encoding said PD-L1 or said peptide fragment; and an adjuvant, for the prevention of, reduction of risk from or treatment of autoimmune diseases. Said autoimmune diseases may preferably be selected from the group consisting of the Coeliac disease, diabetes mellitus type 1 (IDDM), systemic lupus erythematosus (SLE), Sjögren's syndrome, multiple sclerosis (MS), Hashimoto's thyroiditis, Graves' disease, idiopathic thrombocytopenic purpura, and rheumatoid arthritis (RA). Preferably, the autoimmune disease is selected from the group consisting of diabetes, SLE and sclerosis.

Autoimmune Disease Combination Treatment

Current treatments for autoimmune disease are usually immunosuppressive, anti-inflammatory, or palliative. Non-immune therapies, such as hormone replacement in Hashimoto's thyroiditis or diabetes mellitus Type 1 treatment outcomes of the autoaggressive response. Dietary manipulation limits the severity of celiac disease. Steroidal or NSAID treatment limits inflammatory symptoms of many diseases. Intravenous preparations of immune globulin (IVIG) are used for Chronic Inflammatory Demyelinating Polyneuropathy (CIDP) and Guillain-Barré syndrome (GBS). More specific immunomodulatory therapies, such as the TNFα antagonist Etanercept, have been shown to be useful in treating RA. These immunotherapies may be associated with increased risk of adverse effects, such as susceptibility to infection.

Helminthic therapy has developed based on these observations and involves inoculation of the individual with specific parasitic intestinal nematodes (helminths). There are currently two closely-related treatments available, inoculation with either *Necator americanus*, commonly known as hookworms, or *Trichuris* Suis Ova, commonly known as Pig Whipworm Eggs. Research is available that demonstrates this approach is highly effective in treating a variety of autoimmune disorders, including Crohn's, Ulcerative Colitis, Asthma, allergies, Multiple Sclerosis, and chronic inflammatory disorders In an embodiment, the vaccine herein disclosed is used in combination with a second active ingredient such as any of the above mentioned drugs and treatments against autoimmune diseases.

Allergic Inflammation

Allergy is a disorder of the immune system often also referred to as atopy. Allergic reactions occur to environmental substances known as allergens; these reactions are acquired, predictable and rapid. Strictly, allergy is one of four forms of hypersensitivity and is called type I (or immediate) hypersensitivity. It is characterized by excessive activation of certain white blood cells called mast cells and basophils by a type of antibody, known as IgE, resulting in an extreme inflammatory response. Common allergic reactions include eczema, hives, hay fever, asthma, food allergies, and reactions to the venom of stinging insects such as wasps and bees.

Allergic inflammation is an important pathophysiological feature of several disabilities or medical conditions including allergic asthma, atopic dermatitis, allergic rhinitis and several ocular allergic diseases.

It is an object of the present invention to provide a vaccine composition comprising PD-L1 of SEQ ID NO: 1 or a functional homologue thereof having at least 70% identity to SEQ ID NO: 1 or any of the immunogenically active peptide fragments of PD-L1 described herein above or a nucleic acid encoding said PD-L1 or said peptide fragment; and an adjuvant, for the prevention of, reduction of risk from or treatment of allergic inflammation.

Allergic Inflammation Combination Treatment

Two types of treatments are available for the treatment of allergic inflammations, pharmacotherapy and immunotherapy: pharmacotherapy and immunotherapy.

Pharmacotherapy is the use of antagonistic drugs to block the action of allergic mediators, or to prevent activation of cells and degranulation processes. These include antihistamines, cortisone, dexamethasone, hydrocortisone, epinephrine (adrenaline), theophylline, cromolyn sodium and anti-leukotrienes, such as Montelukast (Singulair) or Zafirlukast (Accolate); anti-cholinergics, decongestants, mast cell stabilizers, and other compounds thought to impair eosinophil chemotaxis, are also commonly used.

Immunotherapy is the desensitization or hyposensitization treatment in which the individual is gradually vaccinated with progressively larger doses of the allergen in question. A second form of immunotherapy involves the intravenous injection of monoclonal anti-IgE antibodies. A third type, Sublingual immunotherapy, is an orally-administered therapy which takes advantage of oral immune tolerance to non-pathogenic antigens such as foods and resident bacteria.

In an embodiment, the vaccine herein disclosed is used in combination with a second active ingredient such as any of the above mentioned drugs and treatments against allergic inflammations.

Pharmaceutical Compositions

The present invention regards pharmaceutical compositions capable of treating, reducing the risk of and/or preventing a clinical disorder associated with PD-L1 expression in an individual; in other words the terms vaccine and pharmaceutical composition are used interchangeably herein. The vaccine/pharmaceutical compositions of the present invention may be "traditional" vaccine compositions comprising antigens such as proteins polypeptides and/or nucleic acid molecules. They may also be in the form of compositions comprising cells, such as modified cells originating from the individual and later processed, or to compositions comprising complex molecules such as antibodies or TCRs.

Generally, a vaccine is a substance or composition capable of inducing an immune response in an individual. The composition may comprise one or more of the following: an "active component" such as an antigen(s) (e.g. protein, polypeptides, peptides, nucleic acids and the like), nucleic acid constructs comprising one or more antigens amongst other elements, cells, (e.g. loaded APC, T cells for adoptive transder aso.), complex molecules (Antibodies, TCRs and MHC complexes and more), carriers, adjuvants and pharmaceutical carriers. In the following, the various components of a vaccine composition according to the present invention are disclosed in more detail.

The vaccine composition of the invention is capable of eliciting an immune response against a cancer, DC or APC expressing PD-L1 of SEQ ID NO: 1 or a functional homologue thereof having at least 70% identity to SEQ ID NO 1, when administered to an individual suffering from a cancer and/or infection (leading to the expression of PD-L1). In a preferred embodiment the clinical condition is a cancer. The vaccine composition of the invention is capable of eliciting the production in a vaccinated individual of effector T-cells having a cytotoxic effect against cancer cells, APCs and DCs expressing PD-L1 and/or inducing infiltration of antigen specific T-cells in tumor stroma in a subject.

Antigens and Other Active Components

Protein/Polypeptide Based Vaccine Compositions

The peptides of the present invention preferably bind with high affinity to MHC and are ready for use as antigens as they are presented here. Preferably, the vaccine composition of the present invention comprises one or more of the following: PD-L1 (SEQ ID NO: 1), immunogenically active peptide fragments here from, functional homologues of full length and partial length PD-L1, in particular any of the fragments described herein above. More preferably, the vaccine composition comprises any of the sequences listed in the sequence list of the present disclosure. Very preferably, the vaccine composition comprises the peptides PDL101 (SEQ ID NO: 2), PDL111 (SEQ ID NO: 12), and/or PDL114 (SEQ ID NO: 15).

The choice of antigen in the vaccine composition of the invention will depend on parameters determinable by the person of skill in the art. As it has been mentioned, each of the different peptides of the invention is presented on the cell surfaces by a particular HLA molecule. As such, if a subject to be treated is typed with respect to HLA phenotype, a peptide/peptides are selected that is/are known to bind to that particular HLA molecule. Alternatively, the antigen of interest is selected based on the prevalence of the various HLA phenotypes in a given population. As an example, HLA-A2 is the most prevalent phenotype in the Caucasian population, and therefore, a composition containing a peptide binding to HLA-A2 will be active in a large proportion of that population. Furthermore, the antigens/peptides of the present invention may be modified according to the anchor residue motifs presented in Table 2, to enhance binding to particular HLA molecules.

The composition of the invention may also contain a combination of two or more PD-L1 derived peptides, each interacting specifically with a different HLA molecule so as to cover a larger proportion of the target population. Thus, as examples, the pharmaceutical composition may contain a combination of a peptide restricted by a HLA-A molecule and a peptide restricted by a HLA-B molecule, e.g. including those HLA-A and HLA-B molecules that correspond to the prevalence of HLA phenotypes in the target population, such as e.g. HLA-A2 and HLA-B35. Additionally, the composition may comprise a peptide restricted by an HLA-C molecule.

In the case of peptide-based vaccines, epitopes can be administered in an 'MHC-ready' form, which enables presentation through exogenous loading independently of antigen uptake and processing by host antigen-presenting cells. The peptides of the present invention comprise both peptides in a short 'MHC-ready' form and in a longer form requiring processing by the proteasome thus providing a more complex vaccine composition that can target multiple tumor antigens. The more different HLA groups are targeted by a vaccine, the higher likelihood of the vaccine functioning in diverse populations.

The present invention regards in a preferred embodiment a vaccine composition comprising PD-L1 of SEQ ID NO: 1 or a functional homologue thereof having at least 70% identity to SEQ ID NO: 1 or an immunogenically active peptide fragment comprising a consecutive sequence of said PD-L1 or said functional homologue thereof or a nucleic acid encoding said PD-L1 or said peptide fragment; in combination with an adjuvant for use as a medicament. The vaccine composition may be administered to treat, prevent, or reduce the risk associated with a clinical condition in an individual.

Multi Epitope Vaccine Composition

The invention also relates to highly immunogenic multi-epitope vaccines. Preferably, such vaccines should be designed so as to facilitate a simultaneous delivery of the best-suited PD-L1-derived peptides optionally in combination with other suitable peptides and/or adjuvants as described hereinafter. The present invention encompasses such multiepitope vaccines comprising PD-L1-derived peptides optionally in combination with further proteins or peptides fragments not belonging to or derived from PD-L1 and/or adjuvants as described hereinafter. An important factor driving the development of vaccines having a more complex composition is the desire to target multiple tumor antigens e.g. by designing vaccines comprising or encoding a collection of carefully selected CTL and $T_h$ cell epitopes. The invention thus in one aspect relates to vaccine compositions comprising both Class I and Class II-restricted PD-L1 epitopes.

The peptides of the present invention thus comprise both peptides in a short 'MHC-ready' form (class I restricted), and in a longer form requiring processing by the proteasome (class II restricted). Thus, the composition according to the present invention may be provided as a multi-epitope vaccine comprising class I restricted epitope and/or class II restricted epitopes as defined hereinbefore.

Nucleic Acid Based Vaccine Composition

The vaccine composition according to the present invention may comprise a nucleic acid encoding PD-L1 or an immunologically active peptide fragment thereof, in particular any of the fragments described herein above. Said nucleic acid may thus encode any of the above-mentioned proteins and peptide fragments. The nucleic acid may for example be DNA, RNA, LNA, HNA, PNA, preferably the nucleic acid is DNA or RNA.

The nucleic acids of the invention may be comprised within any suitable vector, such as an expression vector. Numerous vectors are available and the skilled person will be able to select a useful vector for the specific purpose. The vector may, for example, be in the form of a plasmid, cosmid, viral particle or artificial chromosome. The appropriate nucleic acid sequence may be inserted into the vector by a variety of procedures, for example, DNA may be inserted into an appropriate restriction endonuclease site(s) using techniques well known in the art. Apart from the nucleic acid sequence according to the invention, the vector may furthermore comprise one or more of a signal sequence, an origin of replication, one or more marker genes, an enhancer element, a promoter, and a transcription termination sequence. The vector may also comprise additional sequences, such as enhancers, poly-A tails, linkers, polylinkers, operative linkers, multiple cloning sites (MCS), STOP codons, internal ribosomal entry sites (IRES) and host homologous sequences for integration or other defined elements. Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989). The vector is preferably an expression vector, comprising the nucleic acid operably linked to a regulatory nucleic acid sequence directing expression thereof in a suitable cell. Within the scope of the present invention said regulatory nucleic acid sequence should in general be capable of directing expression in a mammalian cell, preferably a human cell, more preferably in an antigen presenting cell.

In one preferred embodiment the vector is a viral vector. The vector may also be a bacterial vector, such as an attenuated bacterial vector. Attenuated bacterial vectors may be used in order to induce lasting mucosal immune responses at the sites of infection and persistence. Different recombinant bacteria may be used as vectors, for example the bacterial vector may be selected from the group consisting of *Salmonella, Lactococcus,* and *Listeria*. In general, induction of immunity to the heterologous antigen HPV16 L1 or E7 could be shown, with strong CTL induction and tumor regression in mice. The vector may furthermore comprise a nucleic acid encoding a T-cell stimulatory polypeptide.

Loaded APCs

In useful embodiments an immunogenic response directed against a cancer disease is elicited by administering the peptide of the invention either by loading MHC class I or class II molecules on antigen presenting cells (APCs) from the individual, by isolating PBMCs from the individual and incubating the cells with the peptide prior to injecting the cells back into the individual or by isolating precursor APCs from the individual and differentiating the cells into professional APCs using cytokines and antigen before injecting the cells back into the individual.

It is thus an aspect of the invention to provide vaccine compositions comprising antigen presenting cells comprising PD-L1 or any of the immunologically active peptide fragment thereof described herein above or a nucleic acid encoding said PD-L1 or said immunologically active peptide fragment. The antigen presenting cell may be any cell capable of presenting an antigen to a T-cell. Preferred antigen presenting cells are dendritic cells. The dendritic cells (DC) may be prepared and used in therapeutic procedure according to any suitable protocol, for example as described herein below. It will be appreciated by the person skilled in the art that the protocol may be adopted to use with individuals with different HLA type and different diseases.

Dendritic cells (DC) may be pulsed with 50 µg/ml HLA-restricted peptide (synthesized at GMP quality) for 1 h at 37° C. peptide and $5 \times 10^6$ cells are administered subcutaneously at day 1 and 14, subsequently every 4 weeks, additional leukapheresis after 5 vaccinations. The generation of DC for clinical use and quality control can be performed essentially as described in Nicolette et al., (2007).

Thus, in one embodiment of the present invention, a method for treating an individual suffering from a clinical condition characterized by the expression of PD-L1, preferably wherein the clinical condition is cancer or an infection, is one wherein the peptide is administered by presenting the peptide to the individual's antigen presenting cells (APCs) ex vivo followed by injecting the thus treated APCs back into the individual. There are at least two alternative ways of performing this. One alternative is to isolate APCs from the individual and incubate (load) the MHC class I molecules with the peptide. Loading the MHC class I molecules means incubating the APCs with the peptide so that the APCs with MHC class I molecules specific for the peptide will bind the peptide and therefore be able to present it to T cells. Subsequently, the APCs are re-injected into the individual. Another alternative way relies on the recent discoveries made in the field of dendritic cell biology. In this case, monocytes (being dendritic cell precursors) are isolated from the individual and differentiated in vitro into professional APC (or dendritic cells) by use of cytokines and antigen. Subsequently, the in vitro generated DCs are pulsed with the peptide and injected into the individual.

Adoptive Immunotherapy/Adoptive Transfer

An important aspect the invention relates to cultivating PD-L1 specific T-cells in vitro and adoptive transfer of these to individuals. Adoptive transfer means that the physician directly transfers the actual components of the immune system that are already capable of producing a specific immune response, into an individual.

It is one objective to the present invention to provide PD-L1 specific T-cells, which may be useful for example for adoptive transfer. Isolated T-cells comprising T-cell receptors capable of binding specifically to PD-L1 peptide/MHC class I or PD-L1 peptide/MHC class II complexes can be adoptively transferred to individuals, said T-cells preferably being T-cells that have been expanded in vitro, wherein the PD-L1 peptide may be any of the PD-L1 peptides mentioned herein above. Methods of expanding T-cells in vitro are well known to the skilled person. The invention also relates to methods of treatment comprising administering T-cells comprising T-cell receptors capable of binding specifically to a MHC-restricted PD-L1 peptide complex to an individual, such as a human being suffering from a cancer disease, wherein the PD-L1 derived peptide may be any of the PD-L1 peptides mentioned herein above. The invention furthermore relates to use of T-cells comprising T-cell receptors capable of binding specifically to PD-L1 or peptide fragments thereof for the preparation of a medicament for the treatment of a cancer or infection. Autologous T-cell transfer may be performed essentially as described in Walter et al., (1995).

TCR Transfer

In yet another embodiment, such T-cells could be irradiated before adoptive transfer to control proliferation in the individual. It is possible to genetically engineer the specificity of T cells by TCR gene transfer (Engels et al., 2007). This allows the transfer of T cells bearing PD-L1 peptide specificity into individuals. In general, the use of T cells for adoptive immunotherapy is attractive because it allows the expansion of T cells in a tumor- or virus-free environment, and the analysis of T cell function prior to infusion. The application of TCR gene-modified T cells (such as T-cells transformed with an expression construct directing expressing of a heterologous TCR) in adoptive transfer has several advantages in comparison to the transfer of T cell lines: (i) the generation of redirected T cells is generally applicable. (ii) High-affinity or very high-affinity TCRs can be selected or created and used to engineer T cells. (iii) High-avidity T cells can be generated using codon optimized or murinized TCRs allowing better surface expression of the stabilized TCRs. Genetic engineering of T cell specificity by T cell receptor (TCR) gene transfer may be performed essentially as described in Morgan et al., (2006).

TCR Transfection

TCR with known anti-tumor reactivity can be genetically introduced into primary human T lymphocytes. Genes encoding TCR alpha and beta chains from a tumor specific CTL clone can be transfected into primary T cells and in this way reprogram T cells with specificity against the tumor antigen. TCR RNA is transfected into PBMC by electroporation (Schaft et al., 2006). Alternatively, T cells can be provided with at new specificity by TCR gene transfer using retroviral vectors (Morgan et al., 2006). However, the provirus from the retroviral vector might integrate at random in the genome of the transfected cells and subsequently disturb cell growth. Electroporation of T cells with TCR-coding RNA overcome this disadvantage, since RNA is only transiently present in the transfected cells and can not be integrated in the genome (Schaft et al., 2006). Furthermore, transfection of cells is routinely used in the laboratory.

Adjuvants and Carriers

The vaccine composition according to the invention preferably comprises an adjuvant and/or a carrier. Examples of useful adjuvants and carriers are given herein below. Thus the PD-L1 of SEQ ID NO:1, the functional homologue thereof or the immunogenically active peptide fragment thereof may in a composition of the present invention be associated with an adjuvant and/or a carrier.

Adjuvants are any substance whose admixture into the vaccine composition increases or otherwise modifies the immune response to the PD-L1 or peptide fragment thereof, see further in the below. Carriers are scaffold structures, for example a polypeptide or a polysaccharide, to which the PD-11 or peptide fragment thereof is capable of being associated and which aids in the presentation of especially the peptides of the present invention.

Many of the peptides of the invention are relatively small molecules and it may therefore be required in compositions as described herein to combine the peptides with various materials such as adjuvants and/or carriers, to produce vaccines, immunogenic compositions, etc. Adjuvants, broadly defined, are substances which promote immune responses. A general discussion of adjuvants is provided in Goding, Monoclonal Antibodies: Principles & Practice (2nd edition, 1986) at pages 61-63. Goding notes, that when the antigen of interest is of low molecular weight, or is poorly immunogenic, coupling to an immunogenic carrier is recommended. Examples of such carrier molecules include keyhole limpet haemocyanin, bovine serum albumin, ovalbumin and fowl immunoglobulin. Various saponin extracts have also been suggested to be useful as adjuvants in immunogenic compositions. It has been proposed to use granulocyte-macrophage colony stimulating factor (GM-CSF), a well-known cytokine, as an adjuvant (WO 97/28816).

A carrier may be present independently of an adjuvant. The function of a carrier can for example be to increase the molecular weight of in particular peptide fragments in order to increase their activity or immunogenicity, to confer stability, to increase the biological activity, or to increase serum half-life. Furthermore, a carrier may aid in presenting the PD-L1 polypeptide or said fragment thereof to T-cells. The carrier may be any suitable carrier known to a person skilled in the art, for example a protein or an antigen presenting cell. A carrier protein could be, but is not limited to, keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diptheria toxoid are suitable carriers in one embodiment of the invention. Alternatively, the carrier may be dextrans for example sepharose.

Thus it is an aspect of the present invention that the vaccine compositions comprise PD-L1 of SEQ ID NO:1, a functional homologue thereof sharing at least 70% sequence identity or any of the immunogenically active peptide fragments described herein above is associated with a carrier such as e.g. a protein of the above or an antigen-presenting cell such as e.g. a dendritic cell (DC).

The vaccine compositions of the invention in general comprise an adjuvant. Adjuvants could for example be selected from the group consisting of: AIK(SO$_4$)$_2$, AlNa (SO$_4$)$_2$, AlNH$_4$ (SO$_4$), silica, alum, Al(OH)$_3$, Ca$_3$(PO$_4$)$_2$, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2% squalene/Tween-80® emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from *Mycobacterium*, tuberculosis, substances found in *Corynebacterium parvum, Bordetella pertussis*, and members of the genus *Brucella*, Titermax, ISCOMS, Quil A, ALUN (see U.S. Pat. Nos. 58,767 and 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21. Preferred adjuvants to be used with the invention include oil/surfactant based adjuvants such as Montanide adjuvants (available from Seppic, Belgium), preferably Montanide ISA-51. Other preferred adjuvants are bacterial DNA based adjuvants, such as adjuvants including CpG oligonucleotide sequences. Yet other preferred adjuvants are viral dsRNA based adjuvants, such as poly I:C. Imidazochinilines are yet another example of preferred adjuvants. The most preferred adjuvants are adjuvants suitable for human use.

Montanide adjuvants (all available from Seppic, Belgium), may be selected from the group consisting of Montanide ISA-51, Montanide ISA-50, Montanide ISA-70, Montanide ISA-206, Montanide ISA-25, Montanide ISA-720, Montanide ISA-708, Montanide ISA-763A, Montanide ISA-207, Montanide ISA-264, Montanide ISA-27, Montanide ISA-35, Montanide ISA 51F, Montanide ISA 016D and Montanide IMS, preferably from the group consisting of Montanide ISA-51, Montanide IMS and Montanide ISA-720, more preferably from the group consisting of Montanide ISA-51. Montanide ISA-51 (Seppic, Inc.) is oil/surfactant based adjuvants in which different surfactants are combined with a non-metabolizable mineral oil, a metabolizable oil, or a mixture of the two. They are prepared for use as an emulsion with an aqueous solution comprising PD-L1 of SEQ ID NO:1, any of the functional homologues thereof described herein above or any of the immunogenically active peptide fragments thereof described herein above. The surfactant is mannide oleate. QS-21 (Antigenics; Aquila Biopharmaceuticals, Framingham, Mass.) is a highly purified, water-soluble saponin that handles as an aqueous solution. QS-21 and Montanide ISA-51 adjuvants can be provided in sterile, single-use vials.

The well-known cytokine GM-CSF is another preferred adjuvant of the present invention. GM-CSF has been used as an adjuvant for a decade and may preferably be GM-CSF as described in WO 97/28816.

It is also contemplated within the invention that the vaccine compositions may comprise more than one different adjuvant and thus the vaccine compositions of the invention may comprise a mixture of the adjuvants mentioned herein above. Furthermore, it is contemplated within the present invention that both the vaccine composition as well as at least one other adjuvant may be administered to an individual in need thereof simultaneously or sequentially in any order.

Desirable functionalities of adjuvants capable of being used in accordance with the present invention are listed in the below table.

TABLE 3

Modes of adjuvant action

| Action | Adjuvant type | Benefit |
| --- | --- | --- |
| 1. Immuno-modulation | Generally small molecules or proteins which modify the cytokine network | Upregulation of immune response. Selection of Th1 or Th2 |
| 2. Presentation | Generally amphipathic molecules or complexes which interact with immunogen in its native conformation | Increased neutralizing antibody response. Greater duration of response |
| 3. CTL induction | Particles which can bind or enclose immunogen and which can fuse with or disrupt cell membranes w/o emulsions for direct attachment of peptide to cell surface MHC-1 | Cytosolic processing of protein yielding correct class 1 restricted peptides Simple process if promiscuous peptide(s) known |
| 4. Targeting | Particulate adjuvants which bind immunogen. Adjuvants which saturate Kupffer cells | Efficient use of adjuvant and immunogen |
| | Carbohydrate adjuvants which target lectin receptors on macrophages and DCs | As above. May also determine type of response if targeting selective |
| 5. Depot Generation | w/o emulsion for short term | Efficiency |
| | Microspheres or nanospheres for long term | Potential for single-dose vaccine |

Source: Cox, J. C., and Coulter, A. R. (1997). Vaccine 15, 248-56.

A vaccine composition according to the present invention may comprise more than one adjuvant. Furthermore, the invention encompasses a therapeutic composition further comprising any adjuvant substance and/or carrier including any of the above or combinations thereof. It is also contemplated that the PD-L1 protein, the functional homologue thereof or any of the immunogenically active peptide fragments thereof, and the adjuvant can be administered separately in any appropriate sequence. Preferably, the vaccine compositions of the present invention comprise a Montanide adjuvant such as Montanide ISA 51 or Montanide ISA 720 or the GM-CSF adjuvant or a mixture thereof.

Accordingly, the invention encompasses a therapeutic composition further comprising an adjuvant substance including any of the above or combinations thereof. It is also contemplated that the antigen, i.e. the peptide of the invention and the adjuvant can be administered simultaneously or separately in any appropriate sequence.

Dosis and Administration

The amount of the PD-L1 or the immunogenically active peptide fragment thereof in the vaccine composition may vary, depending on the particular application. However, a single dose of the PD-L1 or the peptide fragment thereof is preferably anywhere from about 10 μg to about 5000 μg, more preferably from about 50 μg to about 2500 μg such as about 100 μg to about 1000 μg. Modes of administration include intradermal, subcutaneous and intravenous administration, implantation in the form of a time release formulation, etc. Any and all forms of administration known to the art are encompassed herein. Also any and all conventional dosage forms that are known in the art to be appropriate for formulating injectable immunogenic peptide composition are encompassed, such as lyophilized forms and solutions, suspensions or emulsion forms containing, if required, conventional pharmaceutically acceptable carriers, diluents, preservatives, adjuvants, buffer components, etc.

The pharmaceutical compositions may be prepared and administered using any conventional protocol known by a person skilled in the art. In example 2 a non-limiting example of preparation of a vaccine composition according to the invention is given as well as a non-limiting example of administration of such as a vaccine. It will be appreciated by the person skilled in the art that the protocol may be easily adapted to any of the vaccine compositions described herein. In a further embodiment of the invention, the pharmaceutical composition of the invention is useful for treating an individual suffering from a clinical condition characterized by expression of PD-L1, such as cancer and infections.

The immunoprotective effect of the composition of the invention can be determined using several approaches known to those skilled in the art. A successful immune response may also be determined by the occurrence of DTH reactions after immunization and/or the detection of antibodies specifically recognizing the peptide(s) of the vaccine composition.

Vaccine compositions according to the invention may be administered to an individual in therapeutically effective amounts.

The pharmaceutical compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the methods of prophylaxis and treatment with the vaccine composition.

For example, the vaccine compositions can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the vaccine, comprising any of the herein described compounds can be employed as a prophylactic or therapeutic agent. Also any and all conventional dosage forms that are known in the art to be appropriate for formulating injectable immunogenic peptide composition are encompassed, such as lyophilized forms and solutions, suspensions or emulsion forms containing, if required, conventional pharmaceutically acceptable carriers, diluents, preservatives, adjuvants, buffer components, etc.

Preferred modes of administration of the vaccine composition according to the invention include, but are not limited to systemic administration, such as intravenous or subcutaneous administration, intradermal administration, intramuscular administration, intranasal administration, oral administration, rectal administration, vaginal administration, pulmonary administration and generally any form of mucosal administration. Furthermore, it is within the scope of the present invention that the means for any of the administration forms mentioned in the herein are included in the present invention.

A vaccine according to the present invention can be administered once, or any number of times such as two, three, four or five times. In one embodiment the administration of the vaccine composition of the present invention can be administered any number of time such as 1 time monthly the first two years, hereafter administered once every three months for at least two years, such as three years, four years or five years. Administering the vaccine more than once has the effect of boosting the resulting immune response. The vaccine can further be boosted by administering the vaccine in a form or body part different from the previous administration. The booster shot is either a homologous or a heterologous booster shot. A homologous booster shot is a where the first and subsequent vaccinations comprise the same constructs and more specifically the same delivery vehicle especially the same viral vector. A heterologous booster shot is where identical constructs are comprised within different viral vectors.

Second Active Ingredient

It is an aspect of the present invention that the vaccine composition herein provided is used in combination with a second active ingredient. The administration of the vaccine composition and the second active ingredient may be sequential or combined. Examples of second active ingredients are given above for both cancers and infections. It is a further aspect that the vaccine composition may be used in combination with other therapy of relevance for the given clinical condition to be treated. Such therapy may include surgery, chemotherapy or gene therapy, immunostimulating substances or antibodies; a person skilled in the art is able to determine the appropriate combination treatment for a given scenario.

In some cases it will be appropriate to combine the treatment method of the invention with a further medical treatment such as chemotherapy, radiotherapy, treatment with immunostimulating substances, gene therapy, treatment with antibodies and/or antibiotics and treatment using dendritic cells.

Diagnostic and Prognostic Tools

The peptides of the present invention provide the basis for developing widely applicable diagnostic and prognostic procedures in respect of cancer diseases and infections. Thus, in other useful embodiments the composition of the invention is a composition for ex vivo or in situ diagnosis of the presence of PD-L1 expressing cells in an individual. The diagnostic procedure is based on the detection of PD-L1 reactive T cells among PBMCs or in tumor tissue.

Accordingly, there is provided a diagnostic kit for ex vivo or in situ diagnosis of the presence in an individual of PD-L1 reactive T cells among PBMCs or in tumour tissue comprising one or more peptides of the invention, and a method of detecting in an individual the presence of such reactive T cells, the method comprising contacting a tumour tissue or a blood sample with a complex of a peptide of the invention and a Class I or Class II HLA molecule or a fragment of such molecule and detecting binding of the complex to the tissue or the blood cells. In one aspect, the invention provides a complex of a peptide of the invention and a Class I or Class II HLA molecule or a fragment of such molecule, which is useful as a diagnostic reagent such as it is described herein. Such a complex may be monomeric or multimeric.

Another useful diagnostic or prognostic approach is based on generating antibodies in a heterologous animal species, e.g. murine antibodies directed against human PD-L1, which can then be used, e.g. to diagnose for the presence of cancer cells presenting the peptide. For such immunization purposes, the amount of peptide may be less than that used in the course of in vivo therapy, such as that mentioned above. In general, a preferred dose can range from about 1 µg to about 750 µg of peptide. It is also possible to produce monoclonal antibodies based on immunization with a peptide of the invention. Accordingly, the present invention also relates to a molecule, in particular a monoclonal or polyclonal antibody including a fragment hereof, that is capable of binding specifically to a peptide of the invention and to a molecule that is capable of blocking such a binding, e.g. an antibody raised against the monoclonal or polyclonal antibody directed against a peptide of the invention. The invention furthermore relates to isolated T-cell receptors capable of binding specifically to a peptide or a protein of the invention as well as to isolated nucleic acids encoding same. Such T-cell receptors may for example be cloned from protein or peptide specific T-cells using standard techniques well known to the skilled person.

In one aspect the invention also relates to isolated T-cells comprising T-cell receptors capable of binding specifically to PD-L1 and/or any of the immunogenically active peptide fragments thereof described herein. The isolated T-cells may be CD8 T-cells or CD4 T-cells. The isolated T-cells are preferably T-cells that have been expanded in vitro. Methods of expanding T-cells in vitro are well known to the skilled person. Such T-cells may in particular be useful in the treatment of cancer by adaptive transfer or autologous cell transfer. Thus, the invention also relates to pharmaceutical compositions comprising T-cells as well as methods of treatment comprising administering T-cells comprising T-cell receptors capable of binding specifically to PD-L1 or peptide fragments thereof to an individual, in need thereof such as an individual suffering from cancer and/or infections. Autologous cell transfer may be performed essentially as described in Walter et al., (1995).

The present invention provides the means for treating, preventing, alleviating or curing a clinical condition characterized by expression of PD-11 such as cancers and infections preferably a cancer, comprising administering to an individual suffering from the disease an effective amount of a composition as defined herein, a molecule that is capable of binding specifically to a peptide fragment, which may for example be an antibody or a T-cell receptor or the kit-of-parts described herein. Accordingly, it is a further aspect of the invention to provide a method of treating a clinical condition associated with the expression of PD-L1 of SEQ ID NO: 1.

Monitoring Immunization

In preferred embodiments, the pharmaceutical composition of the invention is a vaccine composition. It is therefore of interest, and an aspect of the present invention to monitor the immunization in an individual to whom the vaccine composition of the present invention is administered. The vaccine composition may thus be capable of eliciting an immune response to a cancer and/or infection. As used herein, the expression "vaccine composition" refers to a composition eliciting at least one type of immune response directed against PD-L1 expressing cells such as cancer cells, APCs or DCs. Thus, such an immune response may be any of the following: A CTL response where CTLs are generated that are capable of recognizing the HLA/peptide complex presented on cell surfaces resulting in cell lysis, i.e. the vaccine elicits the production in the vaccinated subject of effector T-cells having a cytotoxic effect against the cancer cells; a B-cell response giving rise to the production of anti-cancer antibodies; and/or a DTH type of immune response. It is on object of the present invention to monitor the immunization of an individual by monitoring any of the above reactions subsequent to administering the composition of the present invention to said individual.

In one aspect the invention relates to methods of monitoring immunization, said method comprising the steps of
  i) providing a blood sample from an individual
  ii) providing PD-L1 of SEQ ID NO:1, any of the functional homologues thereof described herein above or any of the immunogenically active peptide fragments described herein above,
  iii) determining whether said blood sample comprises antibodies or T-cells comprising T-cell receptors specifically binding the protein or peptide
  iv) thereby determining whether an immune response to said protein or peptide has been raised in said individual.

The individual is preferably a human being, for example a human being that has been immunized with PD-L1 or a peptide fragment hereof or a nucleic acid encoding said protein or peptide.

Kit of Parts

The invention also relates to a kit-of-parts comprising
  any of the vaccine compositions described herein and/or
  an PD-L1 of SEQ ID NO:1 or any of the functional homologue hereof described herein above and/or
  any of the immunogenically active polypeptide fragments of PD-L1 described herein above, and/or
  any of the nucleic acids encoding the proteins of the above two bullet points and instructions on how to use the kit of parts.

The invention also relates to a kit-of-parts comprising
  any of the vaccine compositions described herein and/or
  an PD-L1 of SEQ ID NO:1 or any of the functional homologues thereof described herein above and/or
  any of the immunogenically active peptide fragments of PD-L1 described herein above and/or
  any of the nucleic acids encoding the proteins of the above two bullet points
  and a second active ingredient.

Preferably, the second active ingredient is chosen in correspondence with the clinical condition to be treated so that in the case where a cancer is to be treated the second active ingredient is chosen among e.g. chemotherapeutic agents as listed above. Likewise, if treating a microbial/viral infection, the second active ingredient is preferably an anti-biotic and/or an anti-viral agent.

The components of the kit-of-parts are preferably comprised in individual compositions, it is however within the scope of the present invention that the components of the kit-of-parts all are comprised within the same composition. The components of the kit-of-parts may thus be administered simultaneously or sequentially in any order.

EXAMPLES

Example 1

Patients

Peripheral Blood Mononuclear Cells (PBMC) were collected from cancer patients (renal cell carcinoma, melanoma, and breast cancer) and healthy controls. Blood samples were drawn a minimum of four weeks after termination of any kind of anti-cancer therapy. PBMC were isolated using Lymphoprep separation, HLA-typed (Department of Clinical Immunology, University Hospital, Copenhagen, Denmark) and frozen in FCS with 10% DMSO. The protocol was approved by the Scientific Ethics Committee for The Capital Region of Denmark and conducted in accordance with the provisions of the Declaration of Helsinki. Written informed consent from the patients was obtained before study entry.

ELISPOT Assay

The ELISPOT assay was used to quantify peptide specific IFN-γ releasing effector cells as described previously (Andersen et al., 2001, Cancer Res. 61:869-872). In some experiments PBMC were stimulated once in vitro with peptide prior to analysis as described (McCutcheon et al., 1997, *J Immunol Methods* 210:149-166) to extend the sensitivity of the assay. Briefly, nitrocellulose bottomed 96-well plates (MultiScreen MAIP N45; Millipore) were coated overnight with IFN-γ capture mAb (Mabtech). The wells were washed, blocked by X-vivo medium and the effector cells (PBMC collected and when indicated stimulated as described above) were added in duplicates at different cell concentrations, with or without 10 µM peptide. The plates were incubated overnight. The following day, medium was discarded and the wells were washed prior to addition of the relevant biotinylated secondary Ab (Mabtech). The plates were incubated at room temperature (RT) for 2 hours, washed, and Avidin-enzyme conjugate (AP-Avidin; Calbiochem/Invitrogen Life Technologies) was added to each well. Plates were incubated at RT for 1 hour and the enzyme substrate NBT/BCIP (Invitrogen Life Technologies) was added to each well and incubated at RT for 5-10 min. Upon the emergence of dark purple spots, the reaction was terminated by washing with tap water. The spots were counted using the ImmunoSpot Series 2.0 Analyzer (CTL Analyzers).

Establishment of Antigen Specific T-Cell Cultures and Clones

PBMC from a melanoma patient were stimulated with irradiated (20 Gy) autologous PD-L101 peptide-loaded DC (PBMC:DC ratio=3×10$^6$: 3×10$^5$). The following day IL-7 (5 ng/ml) and IL-12 (10 ng/ml) (PeproTech, London, UK) were added. Stimulation of the cultures were carried out every 10 days with PDL101-loaded irradiated autologous DC (2×) followed by IκB10-loaded irradiated autologous PBMC (3×). Hundred and twenty U/ml IL-2 (PeproTech, London, UK) was added after each stimulation. After one month growing cultures were tested for specificity in a standard $^{51}$Cr-release assay.

Cytotoxicity Assay

Conventional $^{51}$Cr-release assays for CTL-mediated cytotoxicity were carried out as described elsewhere (Andersen et al., 1999). Target cells were T2 with and without PDL101 (FIG. 3a) and the HLA-A2+ breast cancer cell line the breast cancer cell line MDA-MB-231 (FIG. 3b) (available at the American Type Culture Collection (ATCC)).

Results

HLA-A2-Restricted, Immune Responses Against PD-L1

The amino acid sequence of the PD-L1 protein was screened for the most probable HLA-A2 nona- and deca-mer peptide epitopes from the main HLA-A2 specific anchor residues (see Table 2). 17 PD-L1 derived peptides were selected and subsequently synthesized. Using the ELISPOT IFN-□□ secretion assay, we examined PBMC from cancer patients and healthy individuals for the presence of specific T-cell responses against these PDL1-derived peptides. PBMC from HLA-A2+, late stage cancer patients (breast cancer, melanoma and renal cell carcinoma) were stimulated once with the different peptides in vitro before examination by ELISPOT. ELISPOT responses were detected against PDL101, (LLNAFTVTV; PD-L1$_{15-23}$, SEQ ID NO:2)), PDL111 (CLGVALTFI; PDL1$_{250-258}$, SEQ ID NO:12) and PDL114 (VILGAILLCL; PDL1$_{242-251}$, SEQ ID NO: 15). In addition, we examined PBMC from healthy individuals for reactivity against these three PDL1 derived peptides. The results are shown in FIG. 1, which shows PDL1 specific spots per 5×10$^5$ PBMC as determined after stimulation once in vitro with peptide as described herein above.

Figure 2:
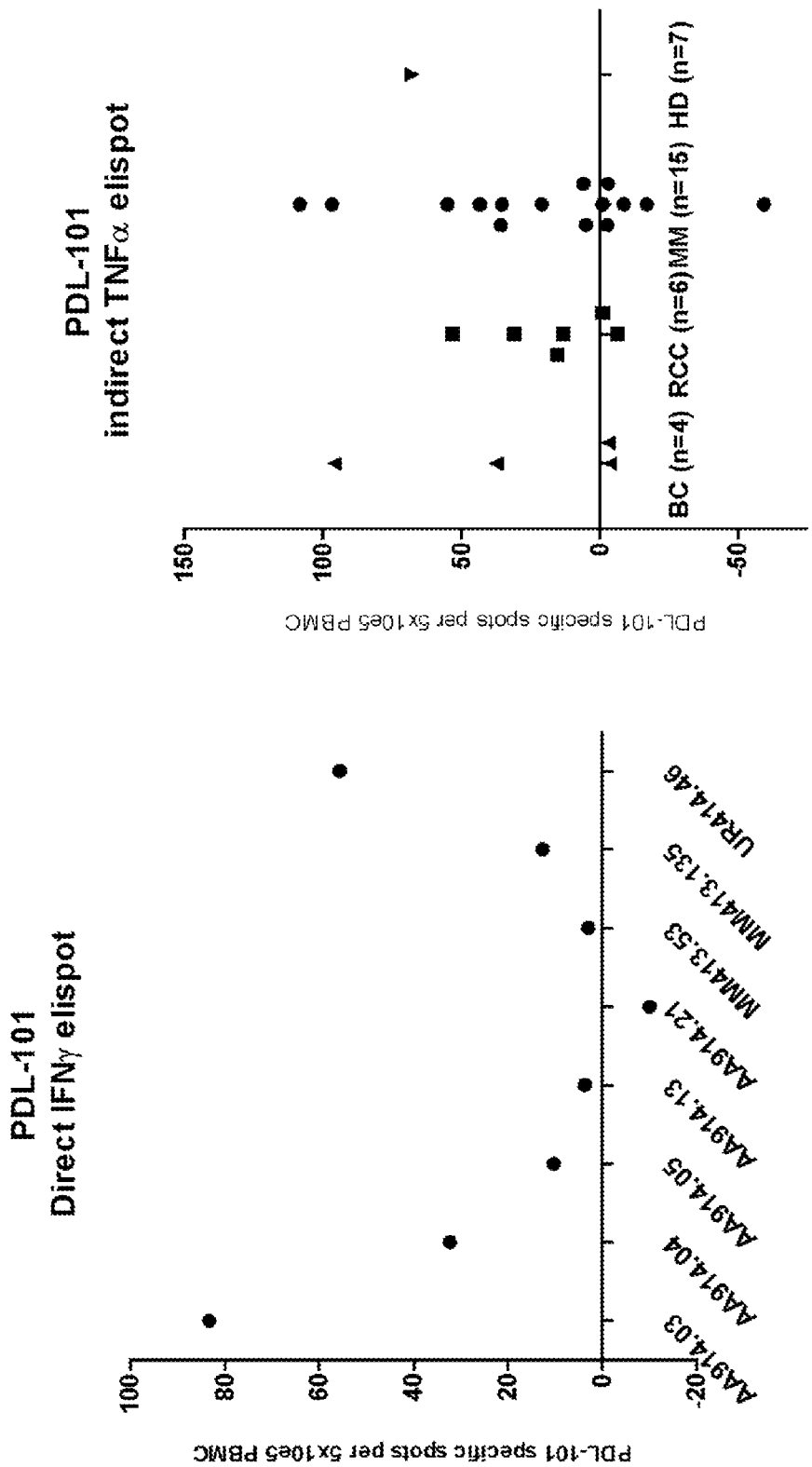
FIG. 2 shows the presence T-cell responses against PDL101 as measured by ELISPOT: (a), The average number of PDL-101 specific spots (after subtraction of spots without added peptide) was calculated per $5 \times 10^5$ PBMC for each patient (white triangle). PBMC from breast cancer patients (BC), renal cell carcinoma patients (RCC), malignant melanoma patients (MM) as well as healthy individuals (HD) were analyzed. PMBC were isolated and plated at $5 \times 10^5$ cells per well in duplicates directly ex vivo in duplicates either without or with the PDL101 peptide. (b), T-cell responses against PDL101 as measured by TNF-α ELISPOT. The average number of PDL-specific spots (after subtraction of spots without added peptide) was calculated per $5 \times 10^5$ PBMC for each patient (white triangle). PBMC from breast cancer patients (BC), renal cell carcinoma patients (RCC), malignant melanoma patients (MM) as well as healthy individuals (HD) were analyzed. T cells were stimulated once with peptide before being plated at $5 \times 10^5$ cells per well in duplicates either without or with the PDL101 peptide.

In addition to determining the presence of specific T-cells using IFNγ as a marker, TNFα was also used as a marker. Thus, an ELISPOT assay was performed essentially as described above with the PDL101 peptide including a stimulation once in vitro with said peptide, except that TNFα antibodies were used in place of IFNγ antibodies. FIG. 2B show the results.

Detection of PD-L1-Reactive HLA-A2-Restricted T Cells in Cancer Patients

While the frequency of PD-L1-reactive T cells are markedly increased by in vitro stimulation, PDL1-reactive T cells were also readily detectable ex vivo in selected patients: In six patients with strong responses after in vitro stimulation, a respective reactivity was also detected ex vivo. The results are shown in FIG. 2A, which shows PDL1 specific spots per 5×10$^5$ PBMC as determined on PBMC directly after collection i.e. without in vitro stimulation.

Functional Capability of PD-L1 Specific T-Cells

Figure 3:
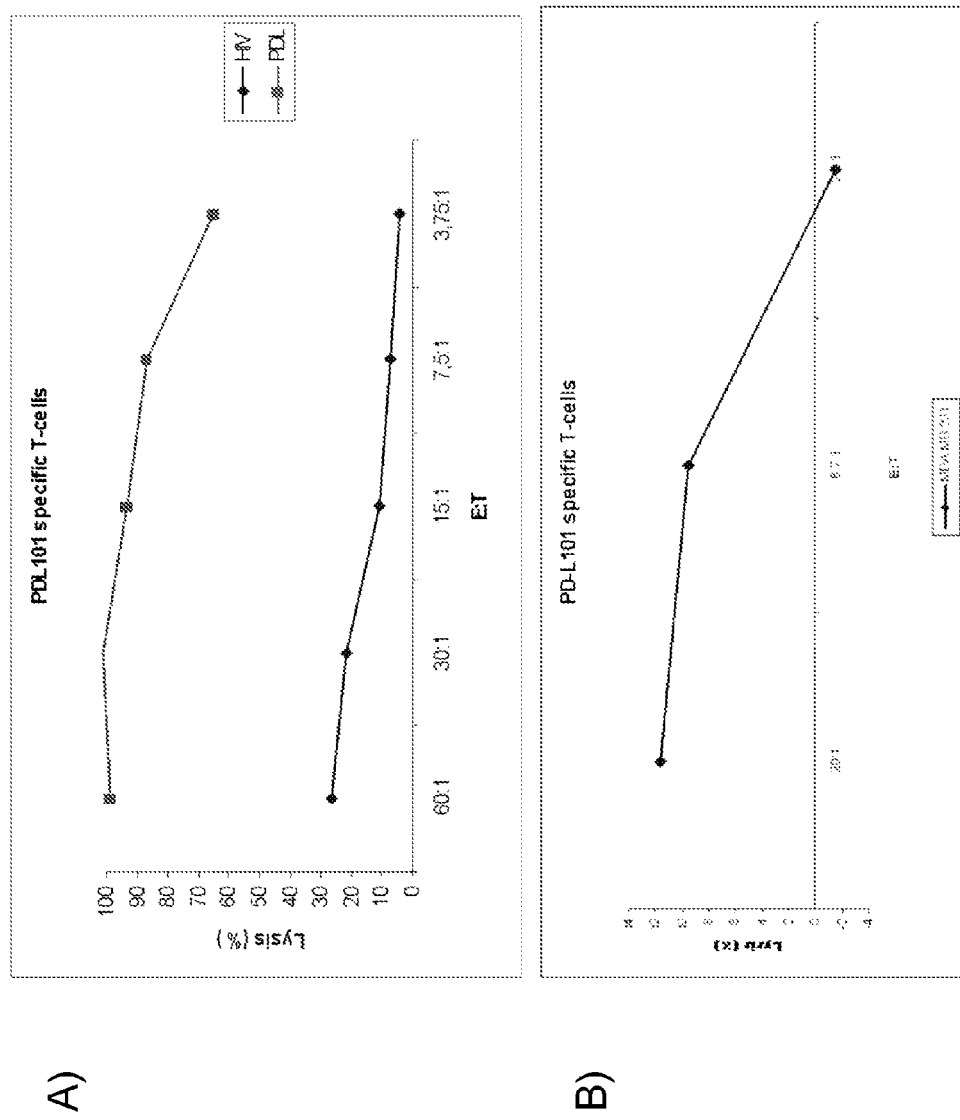
FIG. 3 shows the functional capacity of PDL101-specific T-cells: (a), Lysis by a T-cell bulk culture of T2-cells pulsed with PDL101 peptide (red) or an irrelevant peptide (blue) (HIV-1 $pol_{476-484}$) at different effector to target ratios as measured by $^{51}$Cr-release assay. (b), Lysis of the breast cancer cell line MDA-MB-231 by a T-cell bulk culture at different effector to target ratios as measured by $^{51}$Cr-release assay.

Having identified patients hosting responses against the PDL101 peptide, we used PBMC from such patients to generate specific T-cell cultures against this peptide in vitro. PBMC were stimulated by autologous PD-L1-pulsed Dendritic cells (DC) as described above. After four rounds of stimulation, the peptide specificity was tested in standard $^{51}$Cr-release assays. To this end, either unloaded T2 cells or T2 cells loaded with IκB10 peptide served as targets. This assay revealed that only T2 cells pulsed with PD-L101 were killed (FIG. 3). Next, the PD-L1-specific T cell cultures were further used to test the capacity to kill the HLA-A2 positive cancer cell lines.

Next, CTL clones were established from the specific T-cell cultures by limiting dilution. After a short expansion step, the specificity of the growing clones was analyzed in standard $^{51}$Cr release assays. Clone 9 effectively lysed T2 cells pulsed with PD-L1. Likewise clone 9 generated from the specific bulk culture was able to kill MDA-MB-231 breast cancer cells.

Example 2

Vaccine Composition

500 µg PD-L1 peptide (PDL101, PDL111 or PDL115) in 500 µL phosphate buffer is mixed with 500 µL Montanide adjuvans (Seppic, France) and administered to the patient. In addition 75 µg Leukine (Sargramostim; GM-CSF—available from Genzyme, United States) for stimuluation of the immune system. Both the vaccine composition and the GM-CSF is administered by subcutan injection. The area of vaccination is in addition treated topically with Aldara (Imiquimod—available from MEDA AB, Sweden) to increase the local immune response.

Example 3

Patients

Peripheral Blood Mononuclear Cells (PBMC) were collected from healthy individuals and cancer patients (melanoma, renal cell carcinoma and breast cancer). Blood samples were drawn a minimum of four weeks after termination of any kind of anti-cancer therapy. PBMC were isolated using Lymphoprep separation, HLA-typed and frozen in FCS with 10% DMSO. The protocol was approved by the Scientific Ethics Committee for The Capital Region of Denmark and conducted in accordance with the provisions of the Declaration of Helsinki. Written informed consent from the patients was obtained before study entry.

Prediction of HLA-A2-Binding Peptides from PD-L1

To identify HLA-A2 restricted CTL epitopes for PD-L1, the amino acid sequence of PD-L1 was analyzed using the "Database SYFPEITHIP" (15) available at the internet. The 9mer (here entitled "PD-L101") $PDL1_{15-23}$; (LLNAFTVTV) (SEQ ID NO:2) scored 30 by the SYFPEITHI algorithm and came out as the top candidate epitope. The PD-L101 peptide and two long polypeptides from PD-L1 were produced; PDLong1: $PDL1_{9-28}$, FMTYWHLLNAFTVTVPKDL (SEQ ID NO:23) and PDLong2: $PDL1_{242-264}$, VILGAILLCLGVALTFIFRLRKG (SEQ ID NO:24). Only the former (PDLong1) included the sequence of PD-L101. The HLA-A2 high affinity binding epitope HIV-1 $pol_{476-484}$ (ILKEPVHGV) (SEQ ID NO:20) and CMV pp65 $pos_{495-503}$ (NLVPMVATV) (SEQ ID NO:19) was used as irrelevant controls.

ELISPOT Assay

In the present study the ELISPOT was performed according to the guidelines provided by CIP (http://cimt.eu/cimt/files/dl/cip_guidelines.pdf). In some experiments PBMC were stimulated once in vitro with peptide prior to analysis as described to extend the sensitivity of the assay. Briefly, nitrocellulose bottomed 96-well plates (MultiScreen MAIP N45; Millipore) were coated overnight with the relevant antibodies. The wells were washed, blocked by X-vivo medium and the effector cells were added if possible in triplicates otherwise in duplicates at different cell concentrations, with or without peptide. The plates were incubated overnight. The following day, medium was discarded and the wells were washed prior to addition of the relevant biotinylated secondary Ab (Mabtech), followed by the Avidin-enzyme conjugate (AP-Avidin; Calbiochem/Invitrogen Life Technologies) and finally the enzyme substrate NBT/BCIP (Invitrogen Life Technologies). The spots were counted using the ImmunoSpot Series 2.0 Analyzer (CTL Analyzers). Definition of an ELISPOT response was based on the guidelines and recommendations provided by CIP by an empirical or a statistical approach; the former implies setting a threshold to represent a biological response. This is supported by the CIP guidelines suggesting that a threshold should be defined as >6 specific spots per 100,000 PBMC. The non-parametric Distribution free resampling (DFR) test gives a way of formally comparing antigen stimulated wells with negative control wells. As a minimum the ELISPOT assay must be performed at least in triplets. Furthermore, the non-parametric unpaired Mann-Whitney test was used to compare PD-L101-specific responders between cancer patients and healthy donors.

Establishment of Antigen-Specific T-Cell Cultures

Two PD-L101-specific T cell culture were established. PBMC from a breast cancer patient (CM.21) and from a melanoma (MM.05) patient were stimulated with irradiated PD-L101-loaded autologous DC. The following day IL-7 and IL-12 (PeproTech, London, UK) were added. Stimulation of the cultures were carried out every 8 days with PD-L101 loaded irradiated autologous DC (2×) followed by PD-101 loaded irradiated autologous PBMC. The day after peptide stimulation IL-2 (PeproTech, London, UK) was added.

Generation of DC

DC were generated from PBMC by adherence on culture dishes at 37° C. for 1-2 hr. in RPMI-1640. Adherent monocytes were cultured in RPMI-1640 supplemented with 10% fetal calf serum in the presence of IL-4 (250 U/ml) and GM-CSF (1000 U/ml) for 6 days. DC were matured by addition of IL-β (1000 U/ml), IL-6 (1000 U/ml) TNF-α (1000 U/ml) and $PGE_2$ (1 ug/ml).

Cytotoxicity Assay

Conventional $^{51}$Cr-release assays for CTL-mediated cytotoxicity were carried out as described in Andersen et al., J Immunol 1999. Target cells were T2-cells, HLA-A2$^+$ EBV transformed B-cell line (KIG-BCL), autologous matured DC (mDC), HLA-A2$^+$ melanoma cell lines (MM1312.07 and MM.909.06) with or without IFN-γ (100 U/ml) addition for 2 days. T2-cells and KIG-BCL were pulsed with PD-L1 recombinant protein (Sin θ Biological Inc.) for 3 hr. at 37° C. prior addition of chromium. Lysis of T2-cells was blocked using anti HLA-A2 FITC conjugated antibody (2 ug/100 ul, BD Biosciences).

HLA Peptide Exchange Technology and ELISA

To evaluate the affinity of the HLA-peptide complex a UV exchange method was used in combination with a sandwich ELISA as previously described (19). Two strong binder-peptides (HLA-A2/CMV pp65 $pos_{495-503}$ (NLVPMVATV) (SEQ ID NO:19) and HLA-A2/HIV-1 $pol_{476-484}$ (ILKEPVHGV) (SEQ ID NO:20)) and a sample not exposed to UV light were used as positive controls, while a sample without rescue peptide was used as a negative control. Positive controls were made in quadruplicates and PD-L101 peptide in triplicates.

siRNA Mediated PD-L1 Silencing

Stealth siRNA duplex for targeted silencing of PD-L1 and recommended Stealth siRNA negative control duplex for medium GC content were obtained from Invitrogen (Invitrogen, Paisley, UK). The Stealth PD-L1 siRNA duplex consisted of the sense sequence 5'-CCUACUG-GCAUUUGCUGAACGCAUU3' (SEQ ID NO: 21) and the anti-sense sequence 5'-AAUGCGUUCAGCAAAUGCCA-GUAGG-3' (SEQ ID NO:22). For PD-L1 silencing experiments, mDC were transfected with PD-L1 siRNA using electroporation parameters.

Flow Cytometric Analysis

Flow cytometry analysis was performed on a FACSCANTO II (BD Biosciences, San Jose Calif., USA) to determine PD-L1 surface expression on mDC before and after siRNA targeted silencing, T2-cells, KIG-BCL and HLA-A2$^+$ melanoma cell lines (MM1312.07 and MM.909.06) with or without IFN-γ treatment. Cells were washed in PBS/1% BSA and subsequently stained either with FITC- or PE-Cy5-conjugated anti-PD-L1 monoclonal antibody for 30 min on ice in PBS/1% BSA. Nonreactive isotype-matched antibody (BD Biosciences) was used as control. Fluorescence analyses were performed using FACSDiva software (BD Biosciences) and FlowJo software (Tree Star, Ashland Oreg., USA).

HLA-Multimer Staining

For multimer/tetramer staining, tetramers coupled with PE and APC were prepared using MHC-peptide exchange technology. Staining was performed with CD3-AmCyan, CD8-Pacfic Blue, CD4-FITC (BD Bioscience) and the HLA-tetramer complexes HLA-A2/PD-L101 ($PDL1_{15-23}$; LLNAFTVTV) (SEQ ID NO:2) or HIV-1 ($pol_{476-484}$; ILKEPVHGV) (SEQ ID NO:20) conjugated with APC/PE.

Dead cell marker 7-AAD-PerCP (BD Bioscience) added prior to FACS analysis. For enrichment the T-cell cultures were stained with HLA-A2/PD-L101 tetramer conjugated with PE for and subsequently isolated with anti PE micro beads (MACS Miltenyi Biotec).

In some experiments cells were stimulated with PD-L101 peptide (0.2 mM) or an irrelevant HIV peptide and stained with CD107a-PE antibody (BD Biosciences) for 4 hr. at 37° C. Subsequently, cells were stained with tetramer and surface markers and analysed FACSCANTO II (BD Biosciences, San Jose Calif., USA).

Results

Natural T-Cell Responses Against PD-L1

Figure 4:
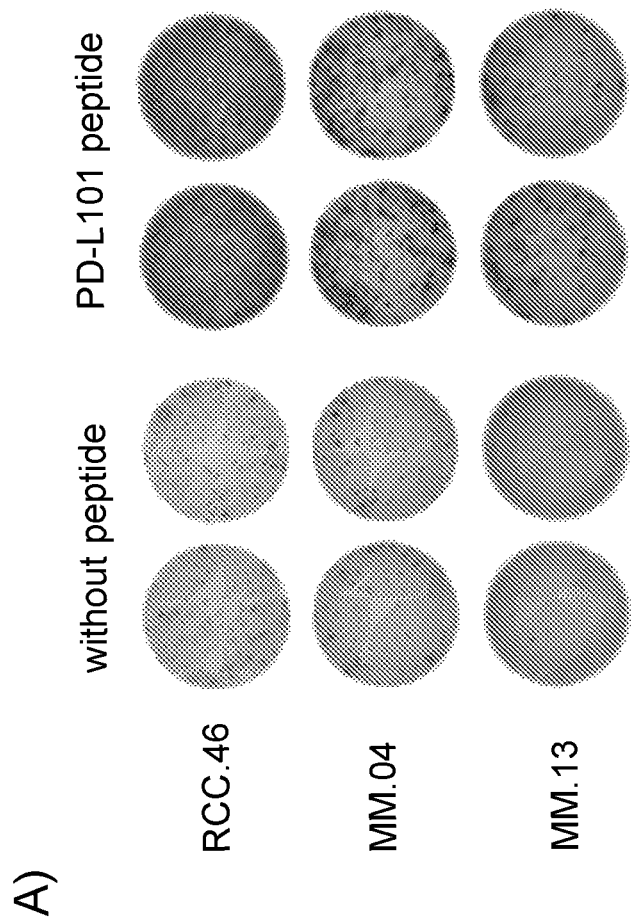
FIG. 4 shows the natural T-cell responses against PD-L1. (A), T-cell responses against PD-L101 peptide (PDL115-23; LLNAFTVTV) (SEQ ID NO:2) as measured by IFN-γ ELISPOT. Examples of ELISPOT responses against PD-L101 for one renal cell carcinoma (RCC) and two malignant melanoma (MM) patients. (B), In total, PBMC from 23 cancer patients and 24 healthy donors, were stimulated once with peptide and screened for responses against PD-L101 using IFN-γ ELIPOT. The average number of PD-L101-specific spots (after subtraction of spots without added peptide) calculated per $5 \times 10^5$ PBMC for each patient. A Mann-Whitney test elucidated a p-value=0.06 with higher frequency of PD-L101 specific T cell responses in cancer patients compared to healthy donors. (C), Examples of IFN-γ ELISPOT in response to PD-L101 (black bars) or without peptide (grey bars) in PBMC from six melanoma patients (MM.03, MM.04, MM.05, MM.13, and MM.135), a breast cancer patient (CM.21), and a renal cell carcinoma patient (RCC.46). (D), INF-α ELISPOT in response to PD-L101 (black bars) or without peptide (grey bars) in PBMC from six melanoma patients (MM.03, MM.04, MM.05, MM.13, and MM.19), a breast cancer patient (CM.21), and a renal cell carcinoma patient (RCC.46). All experiments were performed in triplets and a distribution free resampling (DFR) test confirmed significant responses against PD-L101.
Figure 4:
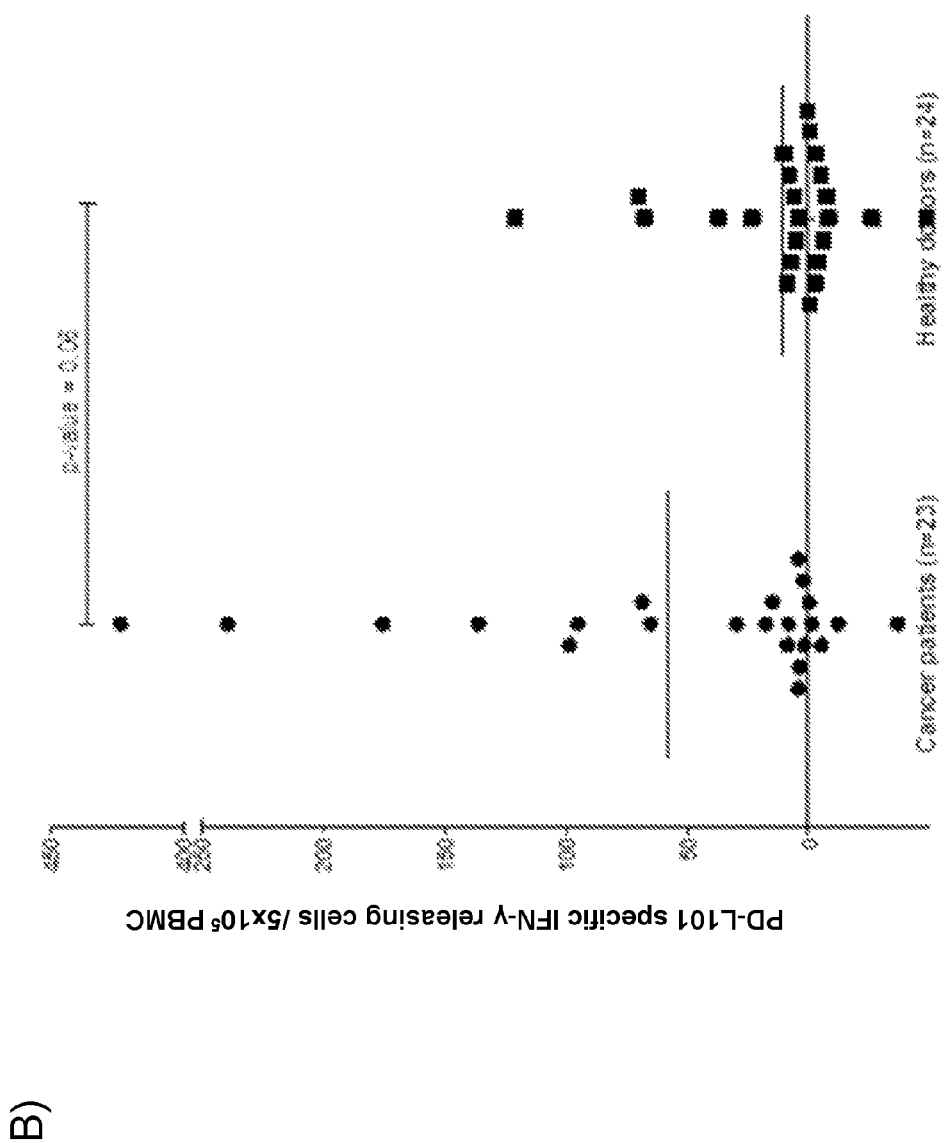
Figure 4:
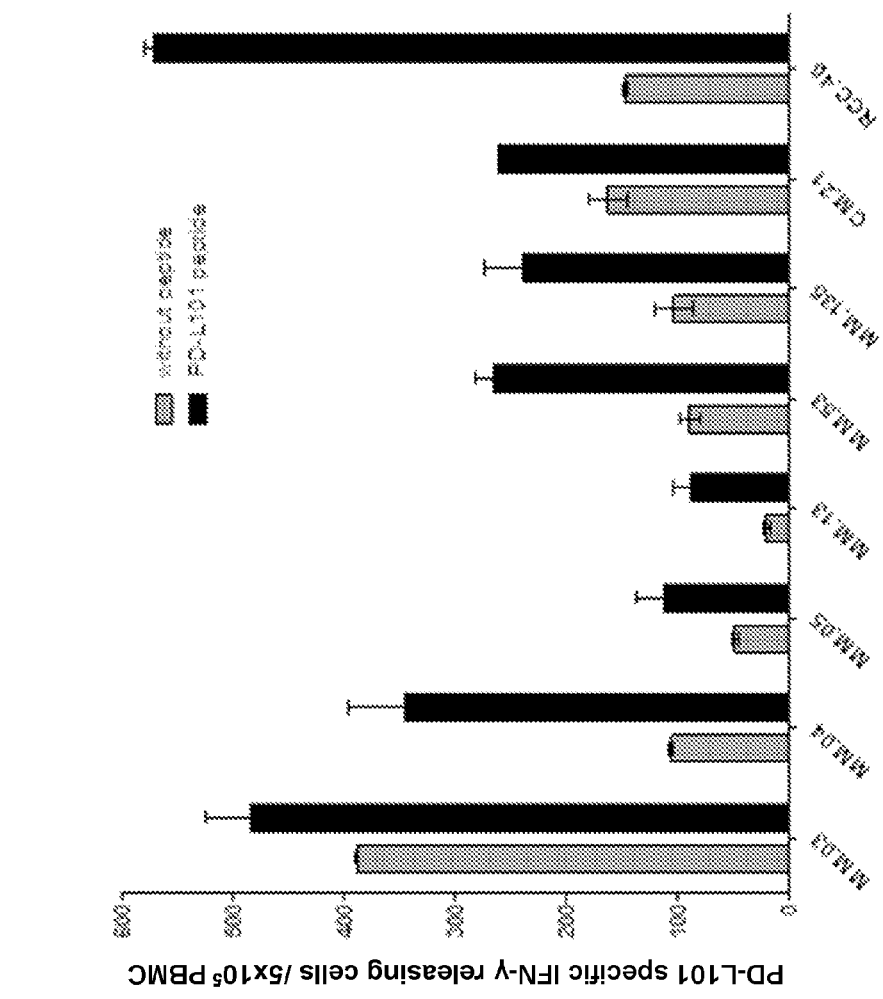
Figure 4:
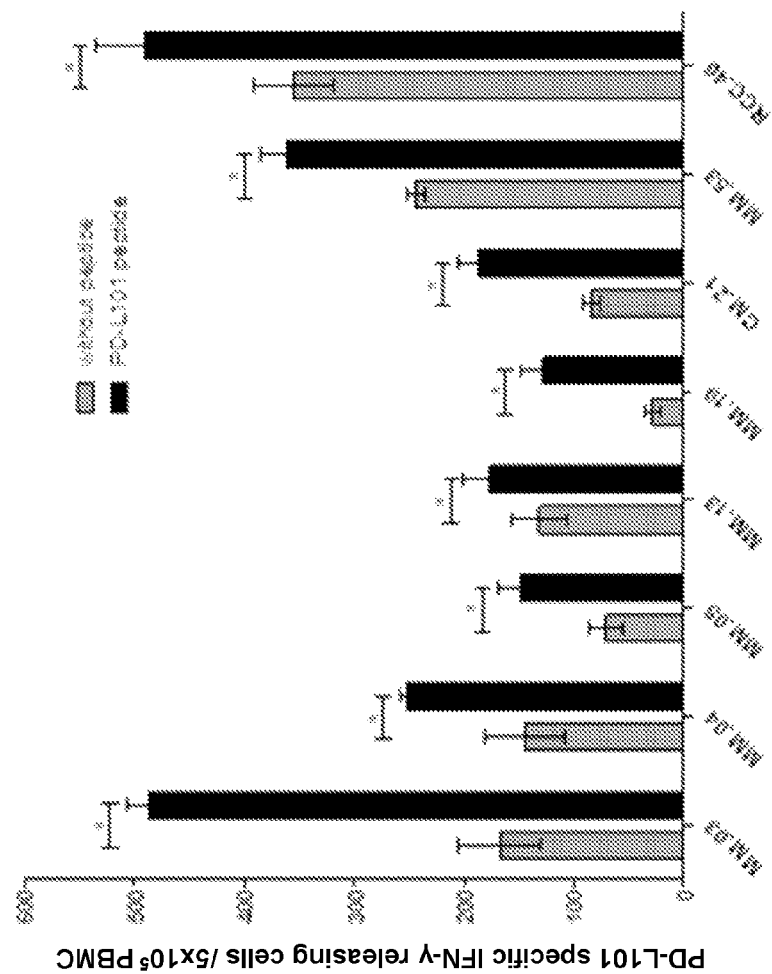

The amino acid sequence of the PD-L1 protein was screened for the most probable HLA-A2 nona- and deca-mer peptide epitopes using the "Database SYFPEITHIP" available at the internet. The peptide PD-L1$_{15-23}$ (LLNAFTVTV) (SEQ ID NO:2) entitled "PD-L101" came out as the top candidate with a predictive score of 30 and this peptide was subsequently synthesized. We scrutinized peripheral blood mononuclear cells (PBMC) from healthy individuals as well as cancer patients for the presence of specific T-cell responses against this PD-L1-derived peptide using the IFN-γ ELISPOT secretion assay. The ELISPOT assay has previously been utilized for the identification of novel tumor antigens based on spontaneous immunity in cancer patients. Thus, HLA-A2$^+$ PBMC from patients with breast cancer, renal cell carcinoma or melanoma were stimulated once with PD-L101 in vitro before examination by ELISPOT. Frequent and strong responses were detected against PD-L101 in several patients. FIG. 4A exemplifies PD-L101-specific T cell responses in one renal cell carcinoma patient (RCC.46) and two melanoma patients (MM.04 and MM.13). Overall, the presence of PD-L1-reactive T cells in the blood of HLA-A2$^+$ cancer patients were revealed by IFN-γ ELISPOT (FIG. 4B). In addition, reactivity against PD-L1 was examined in PBMC from healthy individuals (FIG. 4B). Although PD-L1-specific T cells could be found among PBMC healthy individuals it seemed to be less frequent than in cancer patients, although a Mann-Whitney test illustrated that this difference not quite reached significance (P=0.06). In order to explicate the data, eight responding patients are depicted in a bar plot in FIG. 4C in which responses are compared to background for each patient. The IFN-γ ELISPOT was performed only in duplicates to save material and the responses is, consequently, only considered by the empirical approach as suggested by the CIMT Immuno Guiding Program (CIP) guidelines. We further examined PBMC from PD-L1 IFN-γ-responding patients if PD-L101-specific cells in addition released the cytokine TNF-α. These experiments were performed in triplicates. It can be seen from FIG. 4D that natural PD-L101-specific cells in addition released TNF-α upon stimulation with the PD-L1 derived epitope. In all eight patients the TNF-α response reached significance using a non-parametric Distribution Free Resampling (DFR) test.

Figure 5:
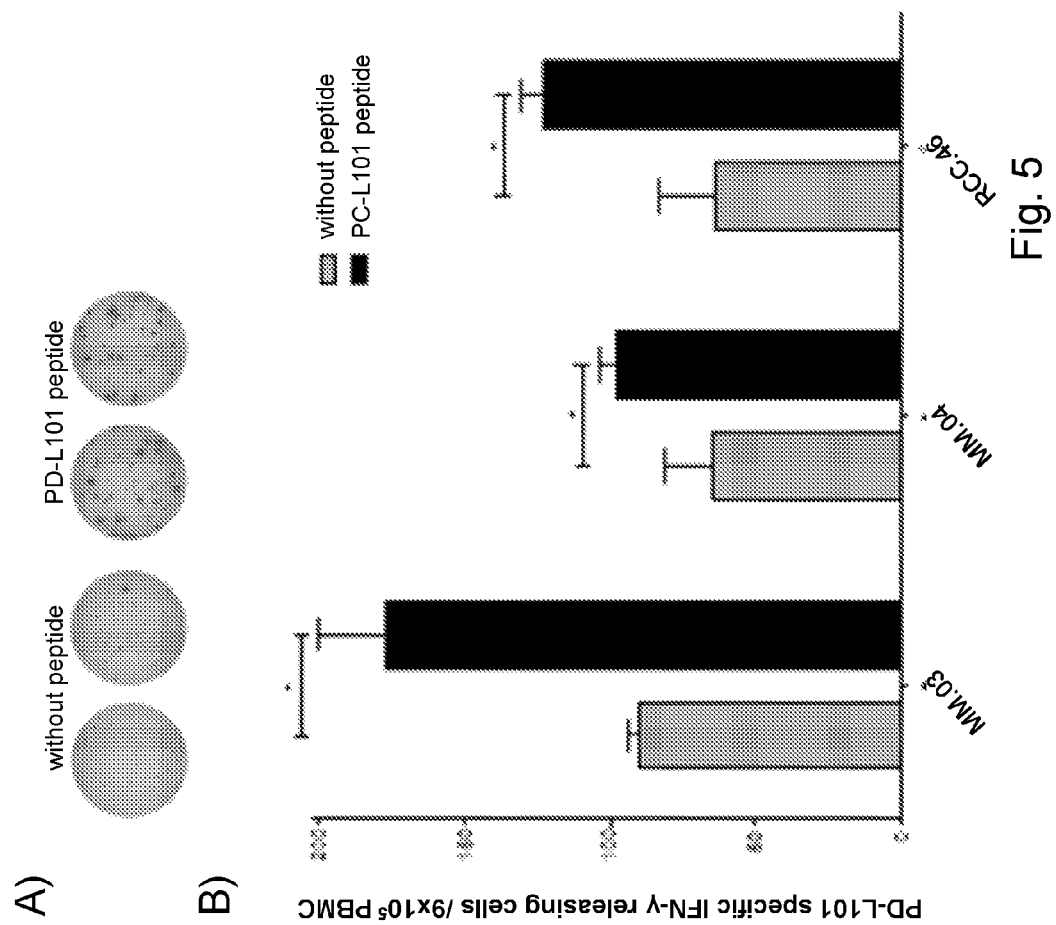
FIG. 5 shows the T-cell responses against PD-L1 ex vivo. (A), Example of a T-cell response against PD-L101 peptide (PDL115-23; LLNAFTVTV) (SEQ ID NO:2) as measured by ex vivo IFN-γ ELISPOT in a melanoma patient (MM.03). (B), Ex vivo IFN-γ ELISPOT in response to PD-L101 (black bars) or without peptide (grey bars) in PBMC from two malignant melanoma (MM.03 and MM.04) and one renal cell carcinoma (RCC.46) patient. All experiments were performed in triplets and a distribution free resampling (DFR) test confirmed significant responses against PD-L101. (C), ELISA analysis of UV-sensitive ligand (KIL-GFVFJV) (SEQ ID NO:28) exchanged with various peptides: CMV/HLA-A2 (pp65 pos495-503; NLVPMVATV) (SEQ ID NO:19), HIV/HLA-A2 (pol476-484; ILKEPVHGV) (SEQ ID NO:20) and PD-L101 (PDL115-23; LLNAFTVTV) (SEQ ID NO:2), No-UV (not exposed to UV light) and No peptide (without rescue peptide). (D), Tetramer analysis of PD-L101-specific T-cells; two example of PD-L101-specific, CD8 T-cells among PBMC from a breast cancer patient (CM.21) (top) and a malignant melanoma patient (MM.05) (bottom) visualised by flow cytometry staining using the tetramers HLA-A2/PD-L101-PE, HLA-A2/HIV-PE as well as the antibody CD8-Pacfic Blue/APC allophycocyanin. The stainings were performed directly ex vivo (left), after one peptide stimulation in vitro (middle) and after three peptide stimulations (right).
Figure 5:
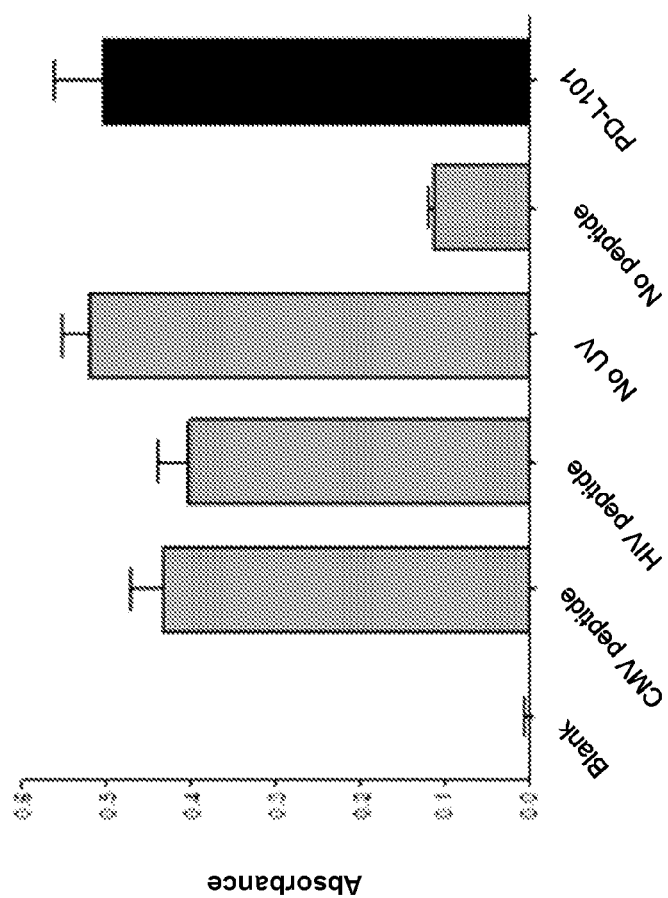
Figure 5:
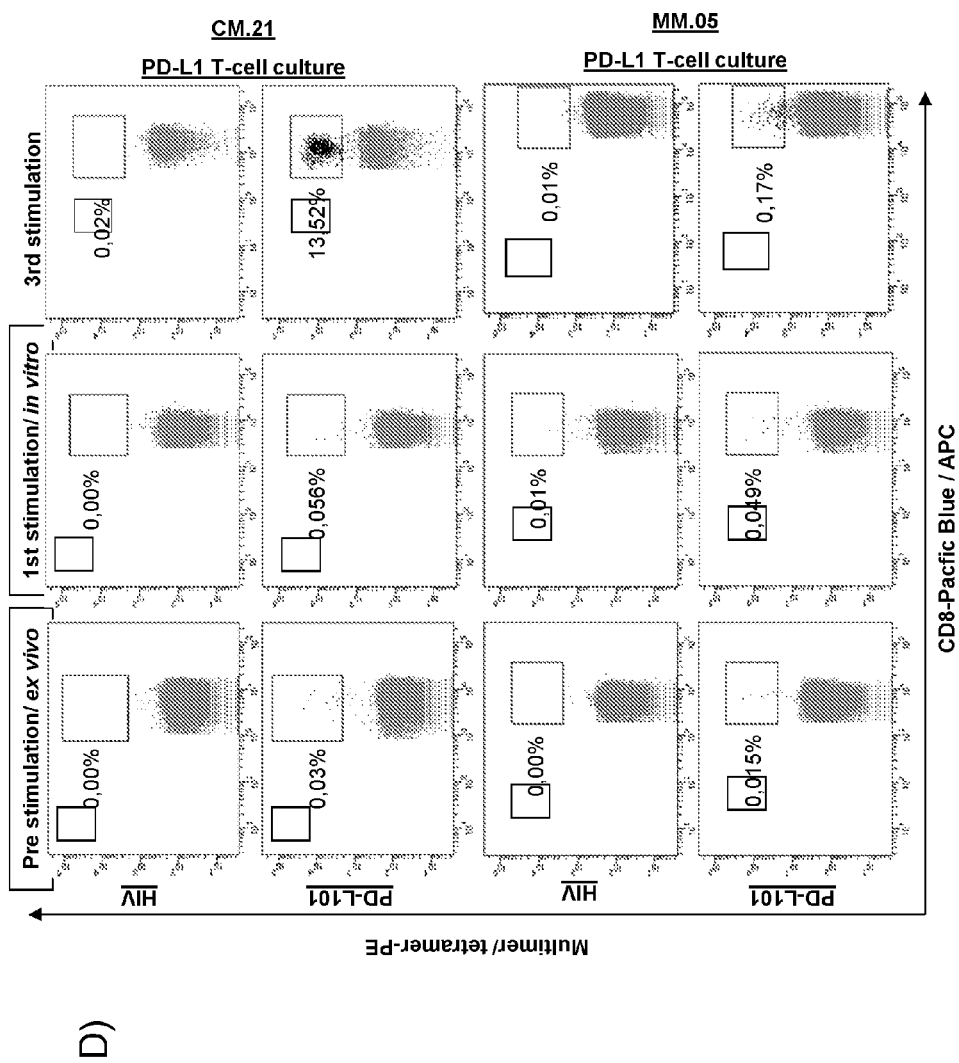

Next, we examined the three responding patients for the presence of PD-L101-specific cells directly ex vivo without peptide stimulation in vitro. A direct ELISPOT is exemplified in FIG. 5A. While the frequency of PD-L1-reactive T cells are markedly increased by in vitro stimulation, PD-L1-reactive T cells were readily detectable ex vivo in selected patients (FIG. 5B).

PD-L101 was examined for its ability to bind to HLA-A2 by the comparison with two HLA-A2-restricted, high affinity epitopes, i.e. HIV-1 pol$_{476-484}$ (ILKEPVHGV) (SEQ ID NO:20) and CMV pp65 pos$_{495-503}$ (NLVPMVATV) (SEQ ID NO:19) using peptide exchange technology followed by ELISA. PD-L101 bound HLA-A2 comparable to the high-affinity control epitope (FIG. 5C). The high binding affinity of PD-L101 to HLA-A2 enabled us to make stable HLA-A2/PD-L101 tetramers, which were used to detect PDL1-reactive CTL by flow cytometry. First, we stained PBMC from two PD-L101-responding patients with the HLA-A2/PD-L101-specific tetramer directly ex vivo. This revealed PD-L1-reactive T cells were detectable ex vivo in both patients (FIG. 5D). In both patients one in vitro peptide stimulation markedly increased the frequency of PD-L1-specific T-cells. Next, we use PBMC from these cancer patients (CM.21 and MM.05) to generate T-cell bulk cultures against this peptide in vitro. Subsequently, we in vitro stimulated PBMC from the patients with PD-L101-pulsed autologous DC. After three in vitro re-stimulations clear HLA-A2/PD-L101-positive T-cells were detectable. 13.52% PD-L1-tetramer positive cells are obtained using T-cells from a breast cancer patient and 0.17% PD-L1-tetramer positive cells are obtained using T-cells from a malignant melanoma patient (FIG. 5D).

PD-L1-Specific T Cells are CTL

Figure 6:
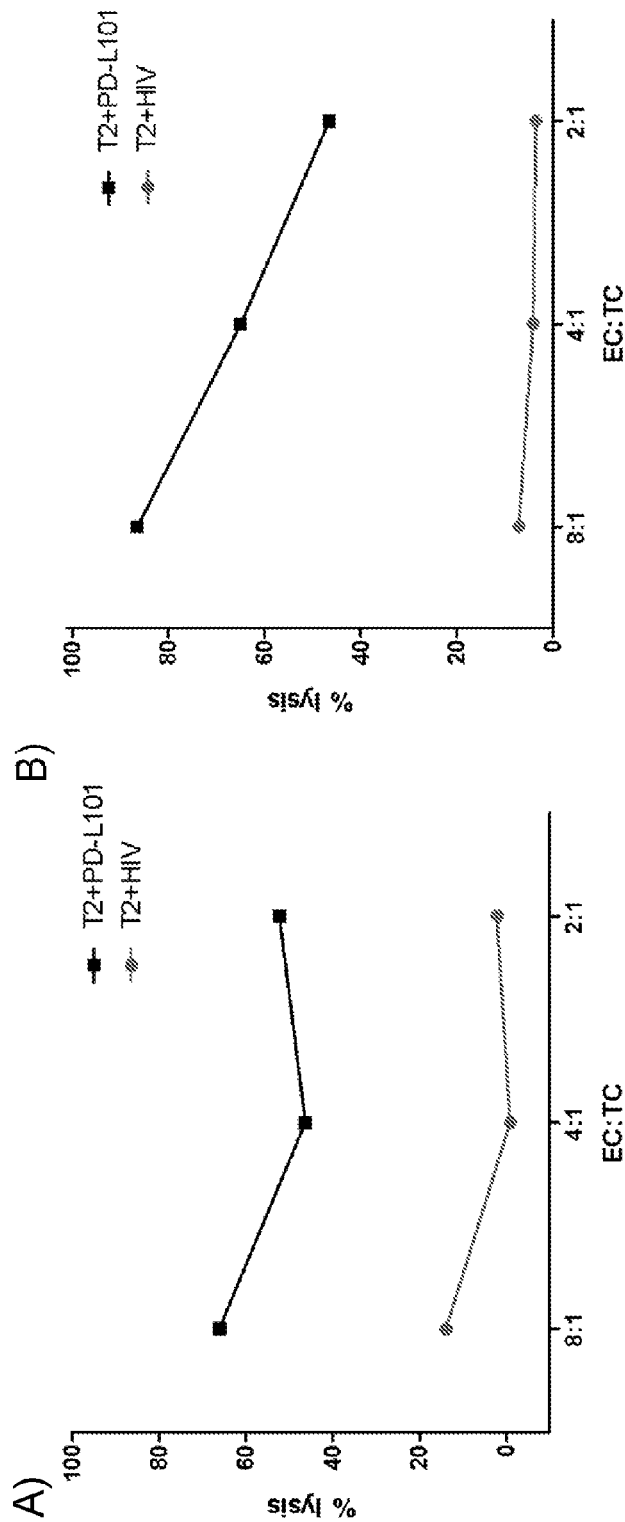
FIG. 6 shows the cytotoxic functionality of PD-L1-specific T cells. (A), $^{51}$Cr-release assay representing % Lysis of T2-cells pulsed with PD-L101 peptide (PDL115-23) or an irrelevant HIV peptide (HIV-1 pol476-484) by CM.21 T-cell culture after third peptide stimulation. (B), Lysis of T2-cells pulsed with PD-L101 peptide (PDL115-23) or an irrelevant HIV peptide (HIV-1 pol476-484) by MM.05 T-cell culture after three peptide stimulation. (C), Cytolytic responses against PD-L101 as measured by GrB ELISPOT. GrB ELISPOT responses are shown in response to PD-L101 (black bars) or without peptide (grey bars) in PBMC from three melanoma patients (MM.03, MM.53 and MM.135). All experiments were performed in triplets and a distribution free resampling (DFR) test showed significant responses against PD-L101 in two of the patients.
Figure 6:
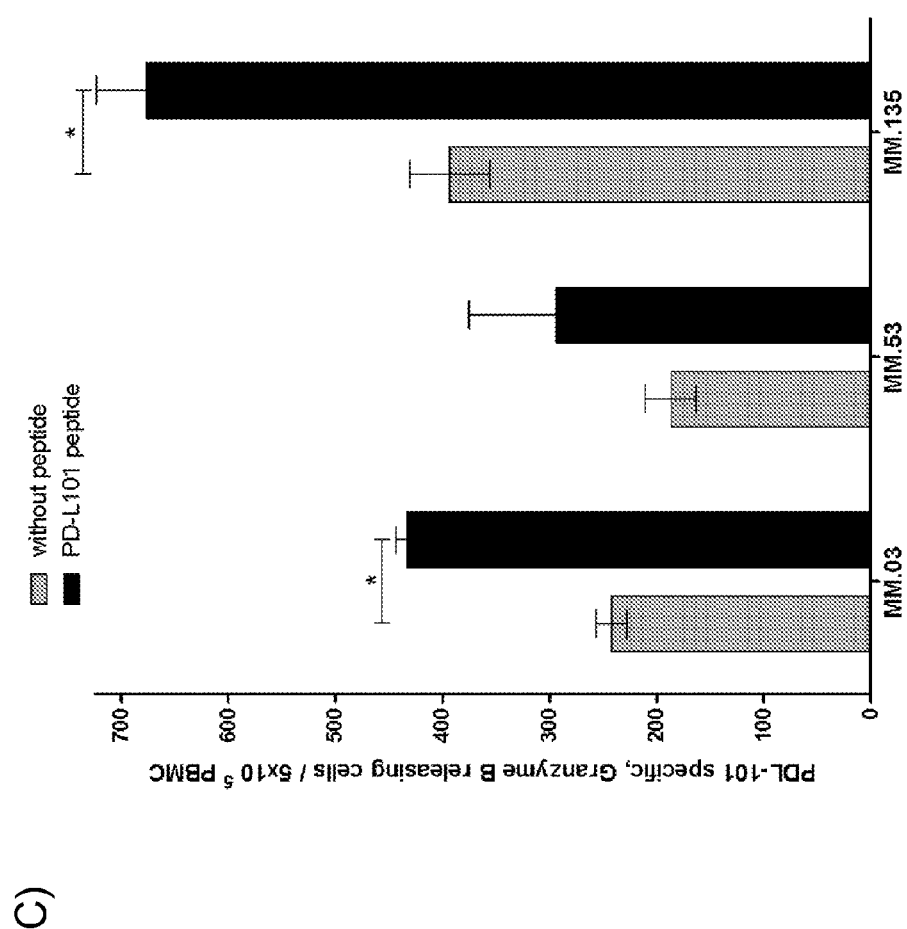

The cytolytic function of the PD-L1-specific cultures was tested in standard $^{51}$Cr release assays using TAP-deficient T2 cells as target cells either loaded with PD-L101 or an irrelevant control peptide from HIV. FIG. 6A illustrates that the T-cell cultures from two different patients lysed T2-cells pulsed with PD-L101 efficiently, whereas no cytotoxic was observed against T2-cells pulsed with the irrelevant peptide. Furthermore, we added either the PD-L101 or the irrelevant HIV peptide directly to the T-cell bulk culture and analysed the culture by FACS. This revealed distinct populations of HLA-A2/PD-L101-tetramer$^+$, CD107a$^+$ cells in cultures with added PD-L101 (FIG. 6B)

Next, we examined if PD-L101-specific T cells present among PBMC directly displayed cytotoxic function. Thus, PBMC from three melanoma patients (MM.03, MM.53 and MM.135) all hosting PD-L101-specific, IFN-γ releasing T cells were analyzed for further reactivity against PD-L101 using the Granzyme B (GrB) ELISPOT. Responses against PD-L101 could be detected in the three patients (although only two reached significance) with a frequency at about 100-300 PD-L101-specific, GrB releasing cells per 5×10$^5$ PBMC (FIG. 6C).

Cytolytic Activity Against PD-L1$^+$ Melanoma Cells

Figure 7:
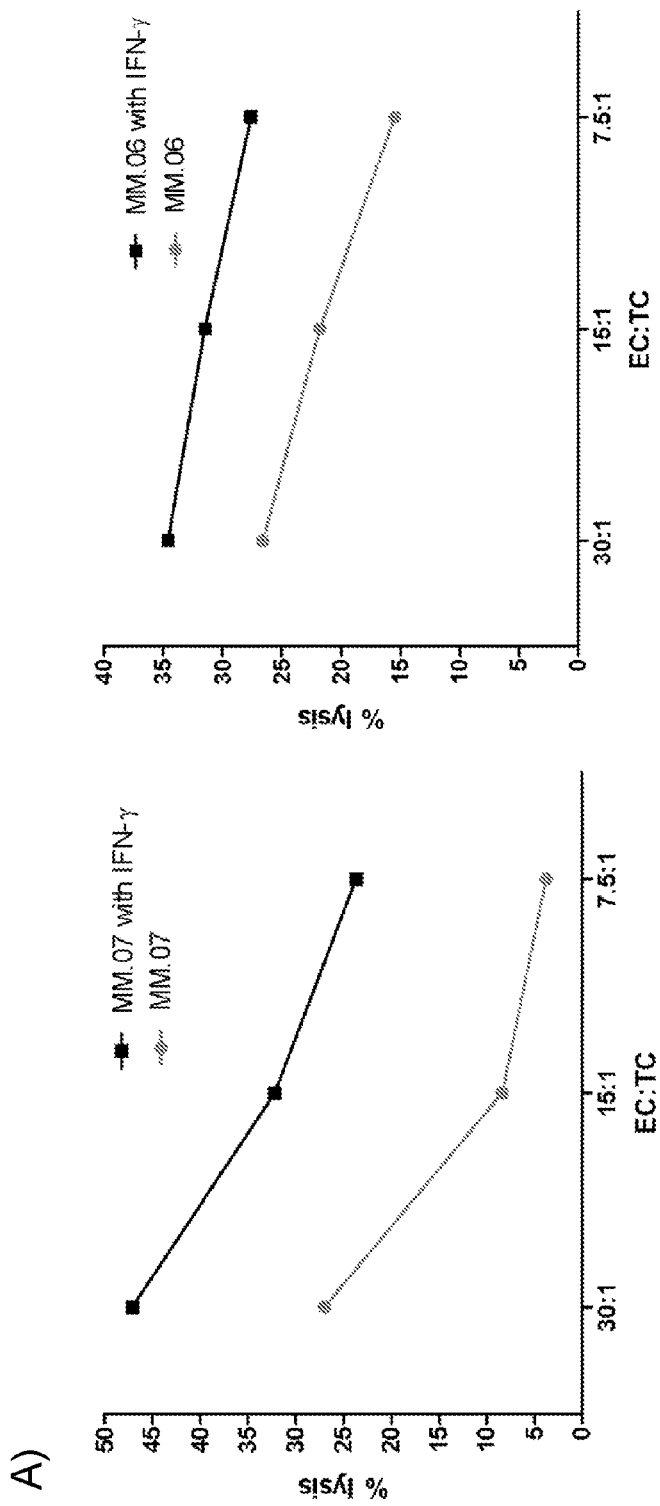
FIG. 7 shows the cytolytic activity against PD-L1+ cancer cells. (A), Lysis of the HLA-A2+ melanoma cell lines MM.06 (left) or MM.07 (right) with or without IFN-γ treatment by a PD-L101-specific T-cell culture (CM.21) at different effector to target ratios as assayed by $^{51}$Cr-release. (B), Histograms showing PD-L1 surface expression on MM.07 and MM.06 with or without IFN-γ treatment. (C), Lysis of the HLA-A2+ melanoma cell lines MM.06 (squares) or MM.07 (circles) by the PD-L101 enriched T-cell culture.
Figure 7:
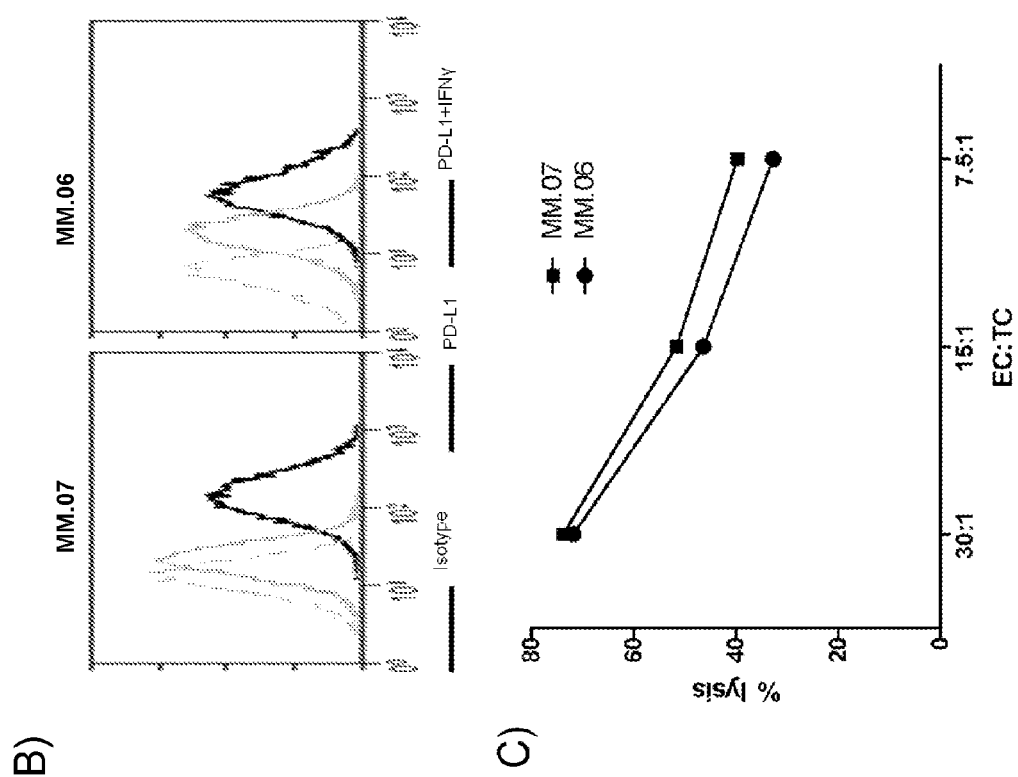

Next, we examined capacity by PD-L101-specific CTL to kill the PD-L1$^+$ melanoma cells MM1312.07 and MM.909.06. A PD-L101-specific CTL culture killed both cell lines, though MM1312.07 was only efficiently killed at an effector to target ratio at 30:1 (FIG. 7A). The CTL culture was highly PDL101 specific. The PD-L1 expression by the two melanoma cell lines MM1312.07 and MM.909.06 were examined by FACS. Both cell lines expressed PD-L1, although MM1312.07 only did exhibit very low expression. IFN-γ treatment increased the expression of PD-L1 in both cell lines (FIG. 7B). In agreement with this, IFN-γ treatment increased the killing of both melanoma cell lines (FIG. 7A). To increase the killing of the recognition of the melanoma cells, we enriched the PD-L101-specific CTL using HLA-A2/PD-L101-tetramer coupled magnetic beads. The resulting CTL culture consisted of about 78% tetramer-positive cells and killed the melanoma cell lines MM1312.07 and MM.909.06 with very high efficiency (FIG. 7C).

PD-L1-Dependent Lysis of Dendritic Cells

Figure 8:
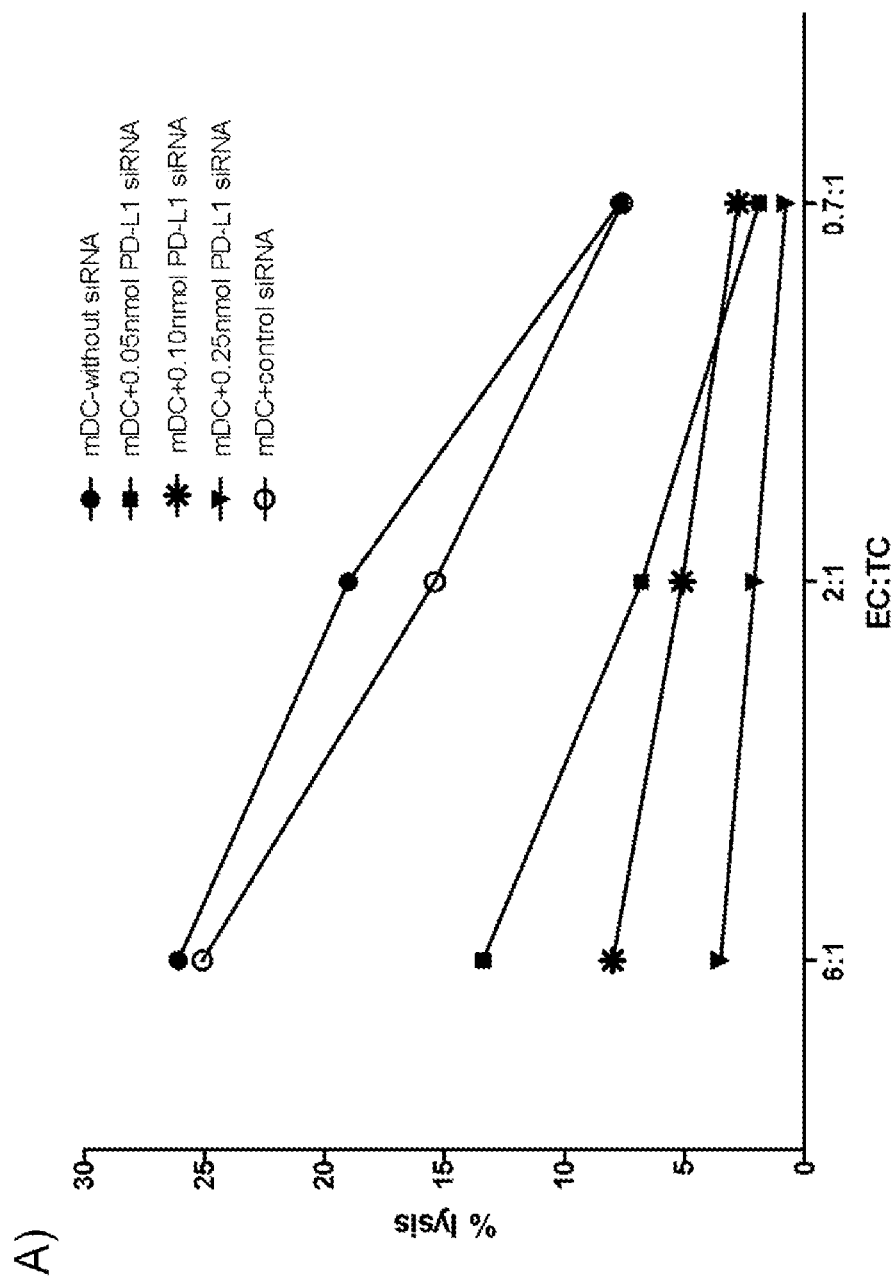
FIG. 8 shows the PD-L1 dependent lysis of dendritic cells. (A-B), The percentage of lysis of autologous mDC without siRNA (black circles), mDC transfected with siRNA against PD-L1 (0.05 nmol (black squares), 0.10 nmol (black stars) and 0.25 nmol (black triangle)) and with control siRNA (white circles) by a PD-L1-specific T-cell culture (top). C), Flow cytometry analysis showing profile of PD-L1 surface expression on mDC without transfection and mDC transfected with siRNA against PD-L1 at three different concentrations (0.05 nmol, 0.10 nmol and 0.25 nmol) and DC transfected with control siRNA.
Figure 8:
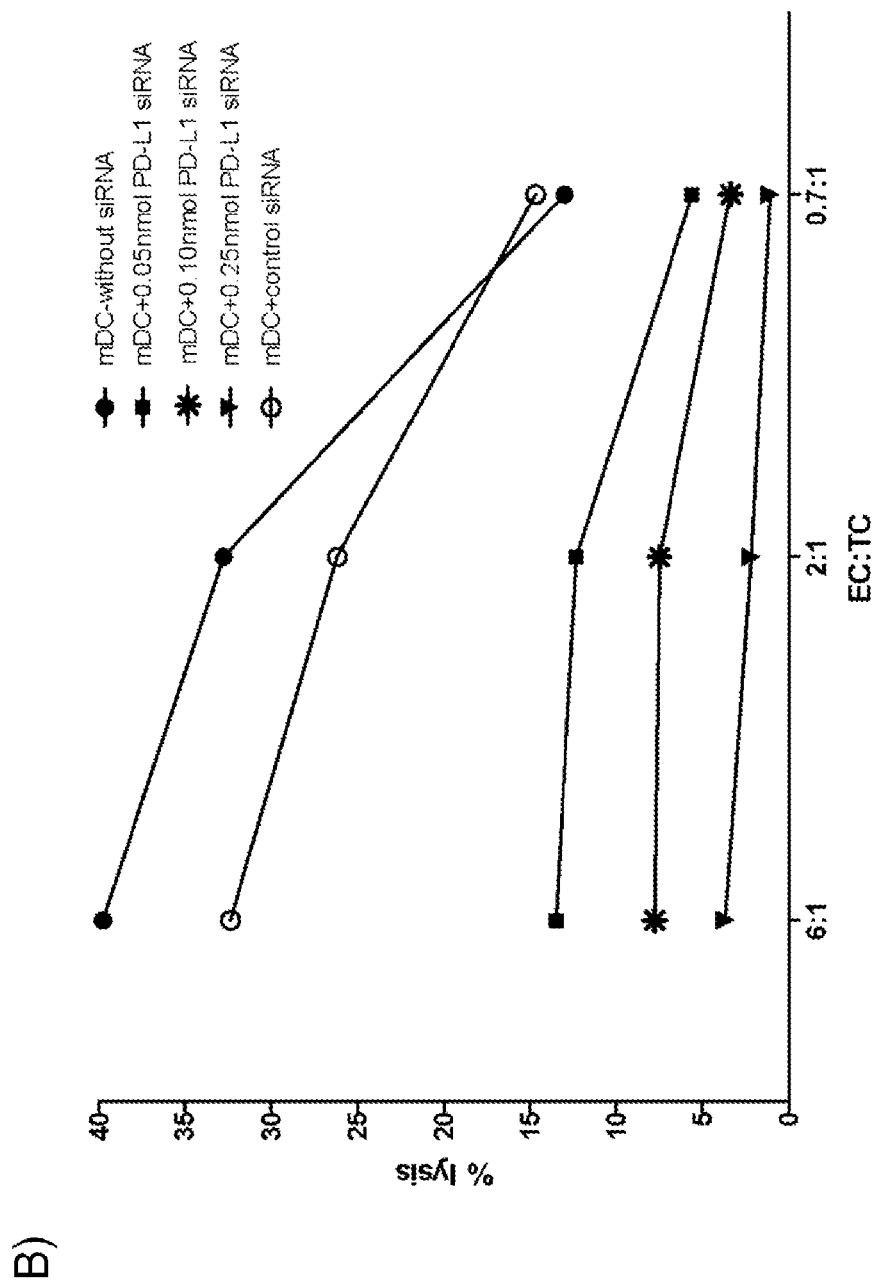
Figure 8:
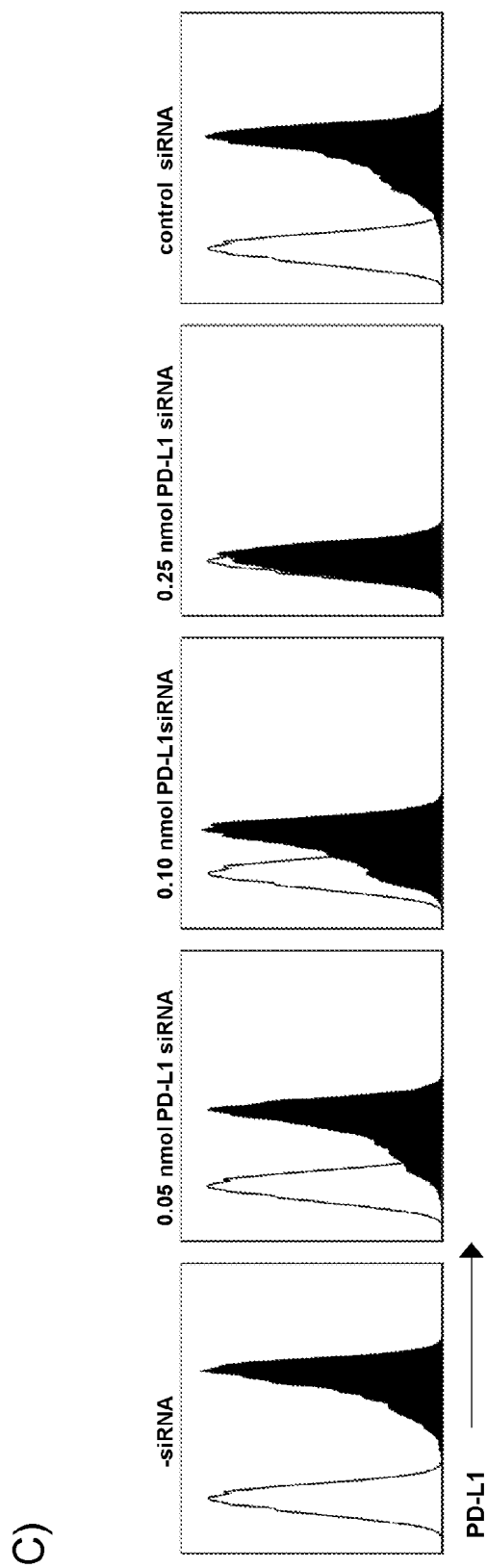

PD-L1 can be induced in immune cells. Thus, as the next and very more important step we addressed the question whether PD-L1-expressing mature DC would also be susceptible for killing by PD-L1-reactive CTL. To test this notion, we generated autologous DC from the same donors from whom the CTL cultures had been generated; the DC were matured by the addition of a standard maturation cocktail consisting of IL-1b, IL-6, TNF-a, and $PGE_2$. We examined two different PD-L101-specific CTL cultures generated from two cancer patients (FIGS. 8A and 8B). Both CTL cultures effectively killed PD-L1 expressing matured DC (mDC) (FIGS. 8A and 8B). Additionally, using different concentrations of PD-L1 siRNA we down-regulated PD-L1 protein expression in the autologous DC and thereby rescued the DC from being killed by the PD-L1-specific CTL cultures (FIGS. 8A and 8B). As control mDC were transfected with medium GC-negative control siRNA. These DC were killed by both PD-L101-specific T-cell cultures (FIGS. 8A and 8B). The percentage of PD-L101-tetramer positive cells among the T-cell cultures killing mDC were assessed by tetramer staining. Tetramer complexes HLA-A2/PD-L101-PE/APC and HLA-A2/HIVPE/APC were used. 46.92% and 71.69% PD-L101-tetramer positive cells among the T-cell cultures killing mDC was identified (FIGS. 8A and 8B respectively). To validate knockdown of PD-L1 on the protein level, we analysed PD-L1 surface expression on mDC 24 hr after siRNA transfection (FIG. 8C). These stainings confirmed that the use of PD-L1 siRNA reduced the level of PD-L1 protein expression in the cells (FIG. 8C) in a concentration dependent matter. Remarkably, the killing efficiency correlated with the amount of PD-L1 expressed by the DC.

Figure 9:
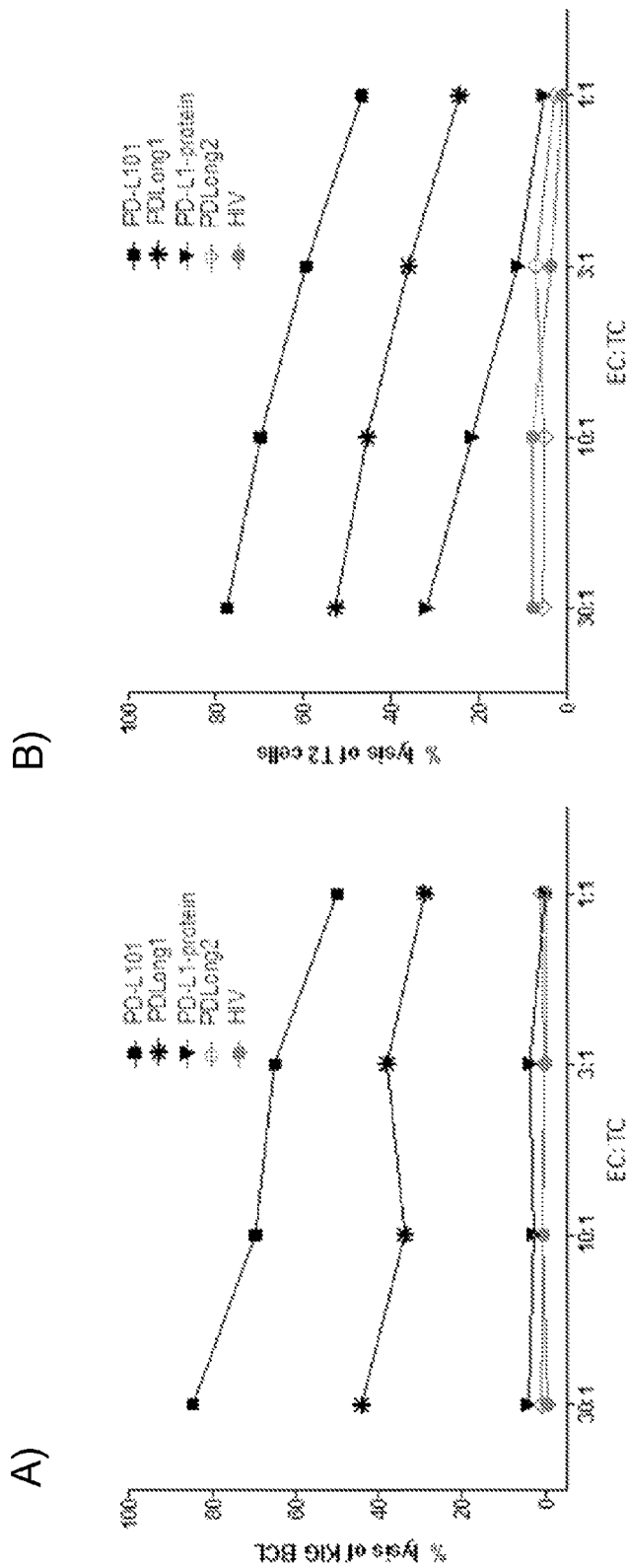
FIG. 9 shows the TAP-independent cross presentation by nonprofessional antigen presenting cells. (A), Lysis of the HLA-A2+ EBV transfected B-cell line (KIG-BCL) pulsed with PD-L101 peptide (PDL115-23) (black squares), PDLong1 (PD-L19-28; FMTYWHLLNAFTVTVPKDL) (SEQ ID NO:23) (black stars), PDLong2 (PDL1242-264; VILGAILLCLGVALTFIFRLRKG) (SEQ ID NO:24) (black triangles), PD-L1 protein (white squares), or an irrelevant HIV peptide (HIV-1 pol476-484) (grey circles) by a PD-L101-specific T-cell culture as measured by standard 51Cr-release (B), Lysis of T2-cells pulsed with PD-L101 peptide (PDL115-23) (black squares), PDLong1 (PD-L19-28; FMTYWHLLNAFTVTVPKDL) (SEQ ID NO:23) (black stars), PDLong2 (PDL1242-264; VILGAILLCL-GVALTFIFRLRKG) (SEQ ID NO:24) (black triangles), PD-L1 protein (white squares), or an irrelevant HIV peptide (HIV-1 pol476-484) (grey circles) by a PD-L101-specific T-cell culture as measured by standard 51Cr-release (C), HLA-A2-restricted killing by PD-L1-specific T-cells was assessed by lysis of T2-cells pulsed with PDLong1 or PDLong1+HLA-A2 blocking antibody. (D), Histograms showing PD-L1 surface expression on KIG-BCL and T2 cell lines.
Figure 9:
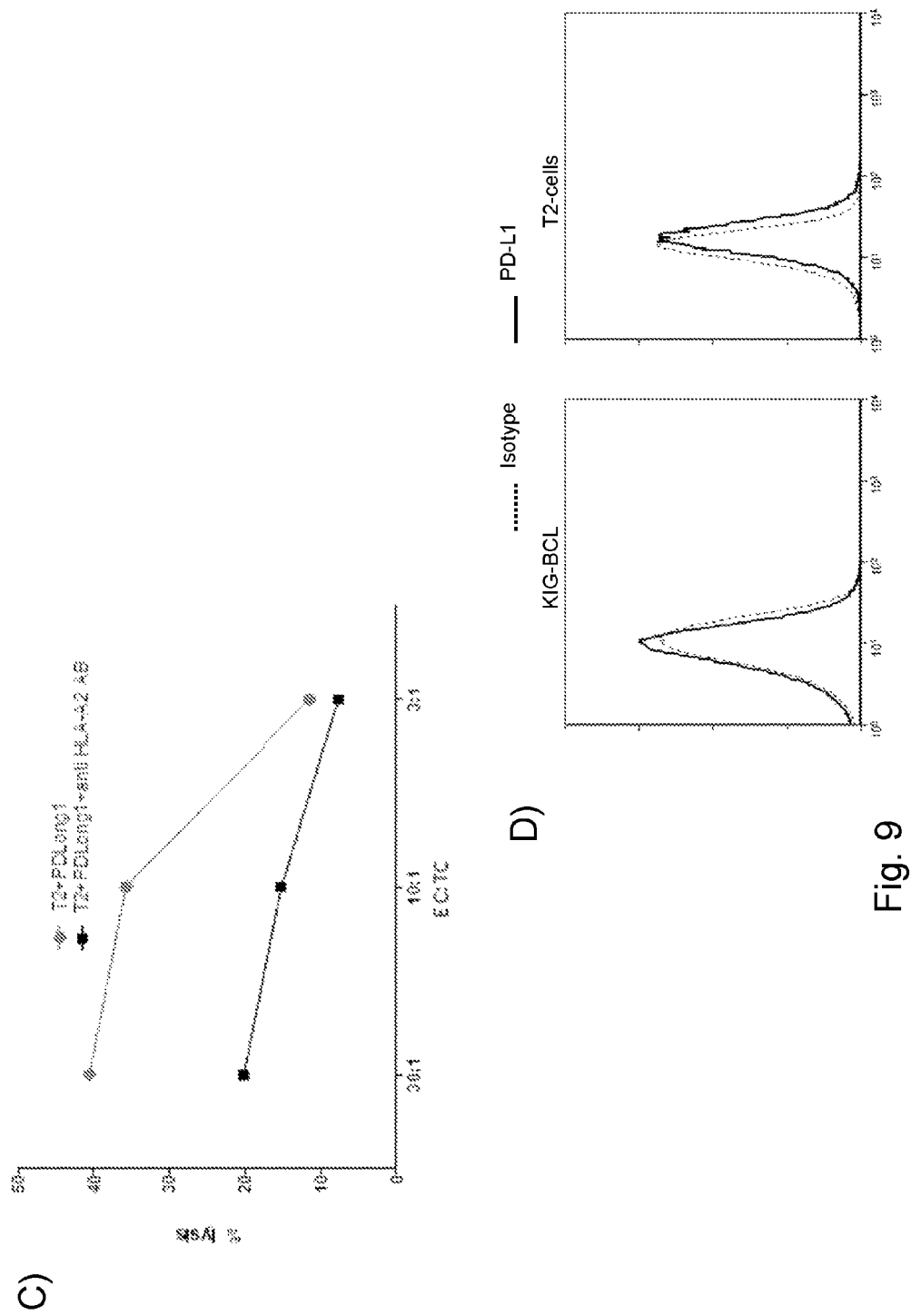

TAP-Independent Cross-Presentation of PD-L1 by Non-Professional Antigen Presenting Cells We analyzed two long polypeptides from PD-L1; $PDL1_{9-28}$ (FMTYWHLLNAFTVTVPKDL) (SEQ ID NO:23) entitled "PDLong1" and $PDL1_{242-264}$ (VILGAILLCLGVALTFIFRLRKG) (SEQ ID NO:24) entitled "PDLong2". Only the former (PDLong1) included the sequence of PD-L101 ($PDL1_{15-23}$; LLNAFTVTV). The PD-L101-specific CTL were tested against the HLA-A2$^+$ EBV transformed B-cell line KIG-BCL pulsed with PD-L101, PDLong1, PDLong2 or an irrelevant HIV peptide. B-cells pulsed not only with the minimal PD-L101 peptide but in addition with PDLong1 peptide were recognized by the PD-L101-specific CTL, whereas B-cells pulsed with either the PDLong2 or HIV control peptides were not killed (FIG. 9A). KIG-BCL cells did not express PD-L1 (FIG. 9D). Similarly, we examined the ability of T2-cells to cross present the long PD-L1 peptide. Thus, the PD-L101-specific CTL were tested against the T2-cells pulsed with PD-L101, PDLong1, PDLong2 or the HIV peptide. Despite the absence of TAP transporters in T2 cells, the PDL01 peptide was efficiently presented by T2-cells, since they were killed by the PD-L101-specific CTL (FIG. 9B). The killing was HLA-A2 restricted, since it could be blocked by the addition of anti-HLA-A2 antibodies (FIG. 9C). T2-cells did not express PD-L1 (FIG. 9D). Finally, we assessed if PD-L101-specific CTL recognized KIG-BCL or T2 cells pulsed with the full length protein for at least 3 hours. KIG-BCL was apparently not able to cross-present the full-length protein, since these cells were not recognized (FIG. 9). Surprisingly, however T2-cells pulsed with the full length protein were recognized and killed by PD-L101-specific CTL (FIG. 9B). Thus, T2-cells were capable not only to take up, process and present PDLong1 but in addition the full-length recombinant PD-L1 protein.

Example 4

To investigate whether co-stimulation with PD-L1 peptide will boost T-cell reactivity against viral and tumor-associated antigens either of the following experiments are performed.

Co-Culturing with Autologous PD-L1-Specific T Cells

PBMC are stimulated in vitro with 50 μg/ml viral peptide (CMV $pp65_{495-503}$ (NLVPMVATV) (SEQ ID NO:19), CMV $1E1_{316-324}$ (VLEETSVML) (SEQ ID NO:25) or Flu matrix $p_{58-66}$ (GILGFVFTL)) (SEQ ID NO:26). 40 U/ml IL-2 is added on day 2 and 6. The PBMC are either cultured alone or with added autologous PD-L1-specific T cells (in a PBMC to PD-L1-specific T cell ratio of 2000:1) on day 6. On day 9, the cultures are stimulated with 120 U/ml IL-2. After 12 days in culture, the number of viral-specific T cells in the cultures, either cultured alone or with added PD-L1-specific T cells are compared by MHC-tetramer staining. The number of Tregs, IL-17A producing T cells and the CD4/CD8 cell ratio in the cultures are also compared. As a control, PBMC are co-cultured with autologous CD8$^+$ T cells of irrelevant specificity.

Co-Stimulation with PD-L1 Peptide

PBMC are stimulated in vitro with 25 μg/ml viral or tumor-associated antigens (CMV $pp65_{495-503}$ (NLVPMVATV) (SEQ ID NO:19), CMV $1E1_{316-324}$ (VLEETSVML) (SEQ ID NO:25), or MART-$1_{26-35}$ (EAAGIGILTV) (SEQ ID NO:27)), either in co-culture with 25 μg/ml PD-L1 peptide or an irrelevant peptide (HIV-1 $pol_{476-484}$ (ILKEPVHGV) (SEQ ID NO:20)). 40 U/ml IL-2 is added every third day. Every seven days, the cultures are stimulated with a mixture of CMV- or MART-1 peptide plus PD-L1 peptide, or a mixture of CMV or MART-1 peptide plus HIV-1 $pol_{476-484}$ peptide, respectively. Cells are stimulated with 10-, 100-, and 1000-fold diluted peptides for the second, third and fourth peptide stimulation, respectively. After three to four stimulations, the number of CMV- or MART-1-specific T cells in the cultures, either co-cultured with PD-L1 peptide or HIV-1 $pol_{476-484}$ peptide, is compared by MHC-tetramer staining. The number of Tregs, IL-17A producing T cells and the CD4/CD8 cell ratio in the cultures are also compared.

The invention claimed is:

1. A vaccine composition comprising:
   a) an immunogenically-active peptide fragment consisting of a consecutive sequence of in the range of 8 to 50 amino acids of the PD-L1 polypeptide of SEQ ID NO: 1, wherein at the most 3 amino acids may be substituted, and wherein said peptide fragment comprises a peptide selected from the group consisting of SEQ ID NO:2, SEQ ID NO:12 and SEQ ID NO:15; and
   b) an adjuvant.

2. The vaccine composition according to claim 1, wherein the vaccine composition comprises an immunogenically active peptide fragment consisting of a consecutive sequence of the polypeptide PD-L1 of SEQ ID NO:1 of in the range of from 8 to 20 amino acids, wherein at the most 2 amino acids may be substituted.

3. The vaccine composition according to claim 1, wherein the vaccine composition comprises an immunogenically active peptide fragment consisting of at the most 40 amino acid residues.

4. The vaccine composition according to claim 1, wherein the vaccine composition comprises an immunogenically active peptide fragment consisting of at the most 20 amino acid.

5. The vaccine composition according to claim 1, wherein the vaccine composition comprises an immunogenically active peptide fragment, wherein said peptide fragment comprises a peptide selected from the group consisting of SEQ ID NO: 2, 12 and 15.

6. The vaccine composition according to claim 1, wherein the vaccine composition comprises an immunogenically active peptide fragment selected from the group consisting of SEQ ID NO: 2, 3 and 4.

7. The vaccine composition according to claim 1, comprising said immunogenically active peptide fragment, wherein said peptide fragment is restricted by a MHC Class I molecule.

8. The vaccine composition according to claim 1, comprising said immunogenically active peptide fragment, wherein said peptide fragment is restricted by a MHC Class II molecule.

9. The vaccine composition according to claim 1, wherein the adjuvant is selected from the group consisting of bacterial DNA based adjuvants, oil/surfactant based adjuvants, viral dsRNA based adjuvants and imidazochinilines.

10. A kit-of-parts comprising:
    (a) the vaccine composition according to claim 1, and
    (b) a composition comprising at least one second active ingredient.

11. A method of treating a clinical condition characterized by the expression of PD-L1, the method comprising administering to an individual suffering from said clinical condition an effective amount of the composition according to claim 1, wherein the clinical condition is cancer.

12. The method according to claim 11, where the cancer is a tumor forming cancer disease.

13. The vaccine composition according to claim 1, wherein the vaccine composition comprises an immunogenically active peptide fragment consisting of at the most 30 amino acid residues.

14. The vaccine composition according to claim 1, wherein the peptide fragment comprises or consists of SEQ ID NO:23.

15. The vaccine composition according to claim 1, wherein the peptide fragment comprises or consists of SEQ ID NO:24.

* * * * *